US012584902B2

(12) United States Patent
Balasubramanian et al.

(10) Patent No.: US 12,584,902 B2
(45) Date of Patent: Mar. 24, 2026

(54) ACOUSTIC SEPARATION OF A TEST SAMPLE

(71) Applicant: Instrumentation Laboratory Company, Bedford, MA (US)

(72) Inventors: Shankar Balasubramanian, Westford, MA (US); Nam Phan, Chelmsford, MA (US); Lara Adib, Chelmsford, MA (US); Yu Wang, Westford, MA (US); Nicholas Vanderslice, Santa Clara, CA (US)

(73) Assignee: Instrumentation Laboratory Company, Bedford, MA (US)

( * ) Notice: Subject to any disclaimer, the term of this patent is extended or adjusted under 35 U.S.C. 154(b) by 262 days.

(21) Appl. No.: 18/534,652

(22) Filed: Dec. 10, 2023

(65) Prior Publication Data

US 2025/0189512 A1    Jun. 12, 2025

(51) Int. Cl.
| | |
|---|---|
| *G01N 33/49* | (2006.01) |
| *G01N 15/14* | (2024.01) |
| *G01N 29/34* | (2006.01) |

(52) U.S. Cl.
CPC ....... *G01N 33/491* (2013.01); *G01N 15/1459* (2013.01); *G01N 29/34* (2013.01)

(58) Field of Classification Search
CPC .. G01N 33/491; G01N 15/1459; G01N 29/34; G01N 1/34; G01N 1/4077; G01N 15/1434; G01N 27/06; G01N 2001/4094; B01L 2200/0652; B01L 2300/0645; B01L 2400/0436; B01L 3/502761
USPC ........................................................ 356/39
See application file for complete search history.

(56) References Cited

U.S. PATENT DOCUMENTS

| | | | |
|---|---|---|---|
| 4,854,170 | A | 8/1989 | Brimhall et al. |
| 5,085,783 | A | 2/1992 | Feke et al. |
| 5,902,489 | A | 5/1999 | Yasuda et al. |
| 6,365,106 | B1 | 4/2002 | Nagai |
| 6,473,172 | B1 | 10/2002 | Pelmulder |
| 6,549,275 | B1 | 4/2003 | Cabuz et al. |
| 6,567,678 | B1 | 5/2003 | Oosta et al. |
| 6,582,963 | B1 | 6/2003 | Weigl et al. |
| 6,587,203 | B2 | 7/2003 | Colon |
| 6,592,821 | B1 | 7/2003 | Wada et al. |

(Continued)

FOREIGN PATENT DOCUMENTS

| | | |
|---|---|---|
| AU | 2016206974 A1 | 7/2017 |
| CA | 2823729 A1 | 7/2013 |

(Continued)

OTHER PUBLICATIONS

Brooks, "2.2.2 Acoustic Properties of Crystal Materials", in "Ultrasonic Inspection Technology Development and Search Unit Design", 2012, pp. 35, 36, 39.

(Continued)

*Primary Examiner* — Md M Rahman
(74) *Attorney, Agent, or Firm* — ArentFox Schiff LLP

(57) ABSTRACT

An example system includes a detector configured to detect a value that is based on a hematocrit of a test sample containing plasma and red blood cells, a fluidic channel configured to hold the test sample, and an acoustic transducer configured to apply acoustic waves to the fluidic channel to separate the plasma from the red blood cells in the fluidic channel. The acoustic waves have at least one of an amplitude, a frequency, or a duration that is based on the value.

19 Claims, 11 Drawing Sheets

(56) References Cited

U.S. PATENT DOCUMENTS

| | | | |
|---|---|---|---|
| 6,597,438 B1 | 7/2003 | Cabuz et al. |
| 6,618,143 B2 | 9/2003 | Roche et al. |
| 6,646,742 B1 | 11/2003 | Gangstead et al. |
| 6,670,191 B2 | 12/2003 | Jiang et al. |
| 6,773,922 B2 | 8/2004 | Jeng et al. |
| 6,784,981 B1 | 8/2004 | Roche et al. |
| 6,825,926 B2 | 11/2004 | Turner et al. |
| 7,003,153 B1 | 2/2006 | Kerofsky |
| 7,016,022 B2 | 3/2006 | Fritz et al. |
| 7,029,628 B2 | 4/2006 | Tam et al. |
| 7,064,823 B2 | 6/2006 | Roche et al. |
| 7,221,453 B2 | 5/2007 | Sharpe et al. |
| 7,248,360 B2 | 7/2007 | Horchner et al. |
| 7,295,310 B2 | 11/2007 | Nieuwenhuis et al. |
| 7,307,721 B2 | 12/2007 | King |
| 7,324,194 B2 | 1/2008 | Roche et al. |
| 7,342,662 B2 | 3/2008 | Harada et al. |
| 7,399,280 B2 | 7/2008 | Liu et al. |
| 7,471,394 B2 | 12/2008 | Padmanabhan et al. |
| 7,484,414 B2 | 2/2009 | Priev et al. |
| 7,542,131 B2 | 6/2009 | Ku |
| 7,544,326 B2 | 6/2009 | Norton et al. |
| 7,564,542 B2 | 7/2009 | Ilkov |
| 7,580,120 B2 | 8/2009 | Hamada et al. |
| 7,628,956 B2 | 12/2009 | Jindo |
| 7,630,063 B2 | 12/2009 | Padmanabhan et al. |
| 7,641,856 B2 | 1/2010 | Padmanabhan et al. |
| 7,671,987 B2 | 3/2010 | Padmanabhan et al. |
| 7,688,427 B2 | 3/2010 | Cox et al. |
| 7,715,006 B2 | 5/2010 | Tabata |
| 7,760,340 B2 | 7/2010 | Hoshiko et al. |
| 7,787,109 B2 | 8/2010 | Dosmann et al. |
| 7,804,594 B2 | 9/2010 | Vacca et al. |
| 7,869,009 B2 | 1/2011 | Dosmann et al. |
| RE42,143 E | 2/2011 | Roche et al. |
| 7,911,617 B2 | 3/2011 | Padmanabhan et al. |
| 7,916,280 B2 | 3/2011 | Ueno et al. |
| 7,972,559 B2 | 7/2011 | Goix et al. |
| 7,978,318 B2 | 7/2011 | Ilkov |
| 7,978,329 B2 | 7/2011 | Padmanabhan et al. |
| 7,981,662 B2 | 7/2011 | Ueno et al. |
| 8,018,592 B2 | 9/2011 | Tabata |
| 8,034,296 B2 | 10/2011 | Cox et al. |
| 8,045,162 B2 | 10/2011 | Vacca et al. |
| 8,064,061 B2 | 11/2011 | Yamamoto et al. |
| 8,071,051 B2 | 12/2011 | Padmanabhan et al. |
| 8,134,705 B2 | 3/2012 | Kaduchak et al. |
| 8,158,439 B2 | 4/2012 | Shibata |
| 8,159,670 B2 | 4/2012 | Vacca et al. |
| 8,194,235 B2 | 6/2012 | Kosaka et al. |
| 8,241,571 B2 | 8/2012 | Goix et al. |
| 8,252,235 B2 | 8/2012 | Shibata et al. |
| 8,253,938 B2 | 8/2012 | Vacca et al. |
| 8,266,950 B2 | 9/2012 | Kaduchak et al. |
| 8,266,951 B2 | 9/2012 | Kaduchak et al. |
| 8,269,952 B2 | 9/2012 | Ueno |
| 8,323,564 B2 | 12/2012 | Padmanabhan et al. |
| 8,383,043 B2 | 2/2013 | Padmanabhan et al. |
| 8,394,338 B2 | 3/2013 | Weis et al. |
| 8,400,632 B2 | 3/2013 | Vacca et al. |
| 8,445,286 B2 | 5/2013 | Bair et al. |
| 8,483,789 B2 | 7/2013 | Higgins |
| 8,522,602 B2 | 9/2013 | Shen et al. |
| 8,524,489 B2 | 9/2013 | Goix et al. |
| 8,540,946 B2 | 9/2013 | Padmanabhan et al. |
| 8,564,764 B2 | 10/2013 | Iwai et al. |
| 8,644,547 B2 | 2/2014 | Hodder et al. |
| 8,714,014 B2 | 5/2014 | Kaduchak et al. |
| 8,715,572 B2 | 5/2014 | Wu et al. |
| 8,741,234 B2 | 6/2014 | Wang et al. |
| 8,741,235 B2 | 6/2014 | Janisch et al. |
| 8,783,109 B2 | 7/2014 | Kaduchak et al. |
| 8,790,592 B2 | 7/2014 | Likuski et al. |
| 8,808,624 B2 | 8/2014 | Matsumoto et al. |
| 8,821,791 B2 | 9/2014 | Shibata et al. |
| 8,841,117 B2 | 9/2014 | Nagai et al. |
| 8,846,406 B1 | 9/2014 | Martin et al. |
| 8,846,408 B2 | 9/2014 | Ward et al. |
| 8,865,003 B2 | 10/2014 | Yang |
| 8,865,074 B2 | 10/2014 | Kwak et al. |
| 8,885,154 B2 | 11/2014 | Wardlaw et al. |
| 8,906,308 B2 | 12/2014 | Krockenberger et al. |
| 8,906,309 B2 | 12/2014 | Krockenberger et al. |
| 8,911,669 B2 | 12/2014 | Krockenberger et al. |
| 8,951,474 B2 | 2/2015 | Takeda |
| 8,963,095 B2 | 2/2015 | Li |
| 8,968,653 B2 | 3/2015 | Fukuma et al. |
| 9,014,430 B2 | 4/2015 | Hodder et al. |
| 9,046,473 B2 | 6/2015 | Levine et al. |
| 9,074,979 B2 | 7/2015 | Kaduchak et al. |
| 9,087,371 B2 | 7/2015 | Muraki |
| 9,097,704 B2 | 8/2015 | Wu et al. |
| 9,103,759 B2 | 8/2015 | Wu et al. |
| 9,110,050 B2 | 8/2015 | Likuski et al. |
| 9,194,785 B2 | 11/2015 | Bentien |
| 9,222,869 B2 | 12/2015 | Chen et al. |
| 9,228,898 B2 | 1/2016 | Kiani et al. |
| 9,261,515 B2 | 2/2016 | Vacca et al. |
| 9,267,931 B2 | 2/2016 | Krockenberger et al. |
| 9,274,054 B2 | 3/2016 | Kendall et al. |
| 9,322,752 B2 | 4/2016 | Wanders et al. |
| 9,377,400 B2 | 6/2016 | Wagner et al. |
| 9,429,524 B2 | 8/2016 | Wanders |
| 9,435,728 B2 | 9/2016 | Tsukii et al. |
| 9,464,977 B2 | 10/2016 | Di et al. |
| 9,470,618 B2 | 10/2016 | Farrell et al. |
| 9,488,621 B2 | 11/2016 | Kaduchak et al. |
| 9,494,570 B2 | 11/2016 | Bransky et al. |
| 9,495,742 B2 | 11/2016 | Lagae et al. |
| 9,500,581 B2 | 11/2016 | Yamada et al. |
| 9,500,584 B2 | 11/2016 | Neijzen et al. |
| 9,506,935 B2 | 11/2016 | Huet et al. |
| 9,513,206 B2 | 12/2016 | Yamada et al. |
| 9,523,670 B2 | 12/2016 | Mueller et al. |
| 9,523,682 B2 | 12/2016 | Huang et al. |
| 9,528,978 B2 | 12/2016 | Yamada |
| 9,551,645 B2 | 1/2017 | Vacca |
| 9,562,858 B2 | 2/2017 | Sano et al. |
| 9,588,036 B2 | 3/2017 | Shinoda |
| 9,594,026 B2 | 3/2017 | Joo et al. |
| 9,595,104 B2 | 3/2017 | Satish et al. |
| 9,651,564 B2 | 5/2017 | Kim et al. |
| 9,652,655 B2 | 5/2017 | Satish et al. |
| 9,656,263 B2 | 5/2017 | Laurell et al. |
| 9,656,265 B2 | 5/2017 | Adolfsen et al. |
| 9,671,326 B2 | 6/2017 | Vacca |
| 9,683,938 B2 | 6/2017 | Ozcan et al. |
| 9,683,984 B2 | 6/2017 | Bransky et al. |
| 9,702,806 B2 | 7/2017 | Wanders et al. |
| 9,719,128 B2 | 8/2017 | Fuchs et al. |
| 9,726,593 B2 | 8/2017 | Kaduchak et al. |
| 9,767,341 B2 | 9/2017 | Ozcan et al. |
| 9,767,343 B1 | 9/2017 | Jones et al. |
| 9,772,274 B2 | 9/2017 | Graham et al. |
| 9,773,320 B2 | 9/2017 | Satish et al. |
| 9,778,163 B2 | 10/2017 | Wu et al. |
| 9,778,167 B2 | 10/2017 | Wagner et al. |
| 9,816,983 B2 | 11/2017 | Fukuma et al. |
| 9,824,441 B2 | 11/2017 | Satish et al. |
| 9,885,665 B2 | 2/2018 | Iversen et al. |
| 9,909,973 B2 | 3/2018 | Wanders et al. |
| 9,920,313 B2 | 3/2018 | Hamman et al. |
| 9,921,147 B2 | 3/2018 | Aubert et al. |
| 9,933,349 B2 | 4/2018 | Vacca et al. |
| 9,939,362 B2 | 4/2018 | Lewis et al. |
| 9,945,769 B2 | 4/2018 | Takeda |
| 10,006,000 B2 | 6/2018 | Grummitt et al. |
| 10,024,779 B2 | 7/2018 | Matsui et al. |
| 10,060,846 B2 | 8/2018 | Wanders et al. |
| 10,073,093 B2 | 9/2018 | Bornheimer et al. |
| 10,094,760 B2 | 10/2018 | Yamada et al. |
| 10,094,761 B2 | 10/2018 | Vacca |
| 10,094,769 B2 | 10/2018 | Hirata et al. |
| 10,101,259 B2 | 10/2018 | Shigaki et al. |

(56) References Cited

U.S. PATENT DOCUMENTS

| | | |
|---|---|---|
| 10,113,966 B2 | 10/2018 | Yamada et al. |
| 10,139,333 B2 | 11/2018 | Kotz et al. |
| 10,151,746 B2 | 12/2018 | Nagai et al. |
| 10,161,849 B2 | 12/2018 | Kimura |
| 10,161,926 B2 | 12/2018 | Gilmanshin et al. |
| 10,180,389 B2 | 1/2019 | Wagner et al. |
| 10,180,398 B2 | 1/2019 | Sinclair |
| 10,190,961 B2 | 1/2019 | Du et al. |
| 10,203,281 B2 | 2/2019 | Sano et al. |
| 10,241,048 B2 | 3/2019 | Izuka et al. |
| 10,254,212 B2 | 4/2019 | Ward et al. |
| 10,254,213 B2 | 4/2019 | Hamada et al. |
| 10,267,721 B2 | 4/2019 | Takeda |
| 10,274,413 B2 | 4/2019 | Heanue et al. |
| 10,282,839 B2 | 5/2019 | Satish et al. |
| 10,337,984 B2 | 7/2019 | Messerschmidt |
| 10,386,290 B2 | 8/2019 | Kaduchak et al. |
| 10,401,350 B2 | 9/2019 | Nagai et al. |
| 10,401,351 B2 | 9/2019 | Nagai et al. |
| 10,422,738 B2 | 9/2019 | Wanders |
| 10,429,292 B2 | 10/2019 | Adams et al. |
| 10,444,222 B2 | 10/2019 | Zhang et al. |
| 10,466,165 B2 | 11/2019 | Graham et al. |
| 10,473,576 B2 | 11/2019 | Perraut et al. |
| 10,473,578 B2 | 11/2019 | Kaduchak et al. |
| 10,481,072 B2 | 11/2019 | Wu et al. |
| 10,481,074 B2 | 11/2019 | Rich |
| 10,488,320 B2 | 11/2019 | Xia et al. |
| 10,509,024 B2 | 12/2019 | Zelmanovic et al. |
| 10,578,541 B2 | 3/2020 | Jooris et al. |
| 10,585,028 B2 | 3/2020 | Calvin |
| 10,613,016 B2 | 4/2020 | Ogumo |
| 10,620,110 B2 | 4/2020 | Du et al. |
| 10,625,259 B1 | 4/2020 | Jones et al. |
| 10,634,602 B2 | 4/2020 | Shi et al. |
| 10,641,644 B2 | 5/2020 | Satish et al. |
| 10,641,698 B2 | 5/2020 | Shi et al. |
| 10,648,898 B2 | 5/2020 | Junnarkar |
| 10,656,069 B2 | 5/2020 | Masuda |
| 10,656,072 B2 | 5/2020 | Vacca |
| 10,663,476 B2 | 5/2020 | Bornheimer et al. |
| 10,705,008 B2 | 7/2020 | Wanders et al. |
| 10,761,007 B2 | 9/2020 | Sieracki et al. |
| 10,798,287 B2 | 10/2020 | Masuda et al. |
| 10,801,007 B2 | 10/2020 | Tabata et al. |
| 10,801,944 B2 | 10/2020 | El-Zehiry et al. |
| 10,816,455 B2 | 10/2020 | Cao et al. |
| 11,231,409 B2 | 1/2022 | Bosy et al. |
| 11,327,048 B2 | 5/2022 | Irving et al. |
| 11,478,796 B2 | 10/2022 | Augustsson et al. |
| 11,656,206 B2 | 5/2023 | Walker et al. |
| 11,959,907 B2 | 4/2024 | Zeng et al. |
| 12,064,765 B2 | 8/2024 | Mehta et al. |
| 12,072,329 B2 | 8/2024 | Zeng et al. |
| 12,092,630 B2 | 9/2024 | Zeng et al. |
| 2002/0028434 A1 | 3/2002 | Goix et al. |
| 2003/0112432 A1 | 6/2003 | Yguerabide et al. |
| 2004/0163970 A1 | 8/2004 | Sin et al. |
| 2005/0106064 A1 | 5/2005 | Laurell et al. |
| 2005/0158704 A1 | 7/2005 | Tyvoll et al. |
| 2007/0098595 A1 | 5/2007 | Tam et al. |
| 2008/0144005 A1 | 6/2008 | Guiney et al. |
| 2008/0291425 A1 | 11/2008 | Norton et al. |
| 2009/0068726 A1 | 3/2009 | Magnin et al. |
| 2010/0009333 A1 | 1/2010 | Auer |
| 2010/0106427 A1 | 4/2010 | Fukuma et al. |
| 2010/0201984 A1 | 8/2010 | Schuda et al. |
| 2010/0255573 A1 | 10/2010 | Bond et al. |
| 2011/0207238 A1 | 8/2011 | Horii et al. |
| 2012/0035061 A1 | 2/2012 | Bransky et al. |
| 2012/0086938 A1 | 4/2012 | Folkenberg |
| 2012/0214224 A1 | 8/2012 | Chan |
| 2012/0218541 A1 | 8/2012 | Barrett et al. |
| 2012/0329082 A1 | 12/2012 | Viola et al. |
| 2013/0020498 A1 | 1/2013 | Ebi et al. |
| 2013/0043170 A1 | 2/2013 | Rose et al. |
| 2013/0048565 A1 | 2/2013 | Fiering et al. |
| 2013/0102863 A1 | 4/2013 | Aknine |
| 2013/0104369 A1 | 5/2013 | Alferness |
| 2013/0112573 A1 | 5/2013 | Noble et al. |
| 2013/0156644 A1 | 6/2013 | Lee et al. |
| 2013/0178724 A1 | 7/2013 | Ting et al. |
| 2013/0324815 A1 | 12/2013 | Jian et al. |
| 2014/0001240 A1 | 1/2014 | Shelton, IV et al. |
| 2014/0008307 A1 | 1/2014 | Guldiken et al. |
| 2014/0011240 A1 | 1/2014 | Lipkens et al. |
| 2014/0147860 A1 | 5/2014 | Kaduchak et al. |
| 2014/0231315 A1 | 8/2014 | Laurell et al. |
| 2014/0273061 A1 | 9/2014 | Wu et al. |
| 2014/0273858 A1 | 9/2014 | Panther et al. |
| 2014/0288400 A1 | 9/2014 | Diab et al. |
| 2014/0291550 A1 | 10/2014 | Jimenez et al. |
| 2014/0295488 A1 | 10/2014 | Konishi et al. |
| 2014/0305196 A1 | 10/2014 | Ellis et al. |
| 2014/0305197 A1 | 10/2014 | Fletcher et al. |
| 2014/0336062 A1 | 11/2014 | Graves et al. |
| 2015/0122997 A1 | 5/2015 | Sandford |
| 2015/0140546 A1 | 5/2015 | James et al. |
| 2015/0177111 A1 | 6/2015 | Warner et al. |
| 2015/0253226 A1 | 9/2015 | Augustsson et al. |
| 2015/0260689 A1 | 9/2015 | Kaduchak et al. |
| 2015/0308971 A1 | 10/2015 | Bisgaard et al. |
| 2015/0346092 A1 | 12/2015 | Lee et al. |
| 2016/0061711 A1 | 3/2016 | Deka |
| 2016/0202237 A1 | 7/2016 | Zeng et al. |
| 2016/0216284 A1 | 7/2016 | Misener et al. |
| 2017/0010210 A1 | 1/2017 | Choung |
| 2017/0227447 A1 | 8/2017 | Degeal et al. |
| 2017/0276591 A1 | 9/2017 | Krockenberger et al. |
| 2017/0326549 A1 | 11/2017 | Jones et al. |
| 2017/0333902 A1 | 11/2017 | Masaeli et al. |
| 2017/0333903 A1 | 11/2017 | Masaeli et al. |
| 2017/0350800 A1 | 12/2017 | Dahlqvist et al. |
| 2017/0363522 A1 | 12/2017 | Yu |
| 2018/0024114 A1 | 1/2018 | Mpock |
| 2018/0049686 A1 | 2/2018 | Marchiarullo et al. |
| 2018/0052147 A1 | 2/2018 | Zeng et al. |
| 2018/0067044 A1 | 3/2018 | Kaduchak et al. |
| 2018/0067135 A1 | 3/2018 | Mpock |
| 2018/0088087 A1 | 3/2018 | Goldschmidt et al. |
| 2018/0106720 A1 | 4/2018 | Schonbrun et al. |
| 2018/0224367 A1 | 8/2018 | Kaduchak et al. |
| 2018/0231451 A1 | 8/2018 | Takeda |
| 2018/0292303 A1 | 10/2018 | Vacca et al. |
| 2018/0298324 A1 | 10/2018 | Takeda et al. |
| 2019/0011350 A1 | 1/2019 | Hayden et al. |
| 2019/0033291 A1 | 1/2019 | Okada et al. |
| 2019/0040356 A1 | 2/2019 | Durack et al. |
| 2019/0054466 A1 | 2/2019 | Gershtein |
| 2019/0056304 A1 | 2/2019 | Gershtein |
| 2019/0056329 A1 | 2/2019 | Low et al. |
| 2019/0056341 A1 | 2/2019 | Low et al. |
| 2019/0056342 A1 | 2/2019 | Low et al. |
| 2019/0094123 A1 | 3/2019 | Cao et al. |
| 2019/0101486 A1 | 4/2019 | Deka |
| 2019/0107476 A1 | 4/2019 | Shi et al. |
| 2019/0128793 A1 | 5/2019 | Shirai et al. |
| 2019/0178782 A1 | 6/2019 | Maekawa et al. |
| 2019/0285639 A1 | 9/2019 | Connolly et al. |
| 2019/0290829 A1 | 9/2019 | Fiering et al. |
| 2019/0310180 A1 | 10/2019 | Heanue et al. |
| 2019/0339189 A1 | 11/2019 | Takeda et al. |
| 2019/0346364 A1 | 11/2019 | Brunelle |
| 2019/0361008 A1 | 11/2019 | Laugharn et al. |
| 2019/0368999 A1 | 12/2019 | Kambayashi et al. |
| 2020/0033249 A1 | 1/2020 | Adams et al. |
| 2020/0049616 A1 | 2/2020 | Watson et al. |
| 2020/0064254 A1 | 2/2020 | Vanderklein et al. |
| 2020/0072794 A1 | 3/2020 | Kaduchak et al. |
| 2020/0072795 A1 | 3/2020 | Kaduchak et al. |
| 2020/0080926 A1 | 3/2020 | Wanders et al. |
| 2020/0080994 A1 | 3/2020 | Brunelle |
| 2020/0103395 A1 | 4/2020 | Bosy et al. |
| 2020/0116673 A1 | 4/2020 | Walker et al. |

(56) References Cited

U.S. PATENT DOCUMENTS

| | | | |
|---|---|---|---|
| 2020/0116698 A1 | 4/2020 | Zelmanovic et al. |
| 2020/0132586 A1 | 4/2020 | Johnson |
| 2020/0141858 A1 | 5/2020 | Wu et al. |
| 2020/0158615 A1 | 5/2020 | Shi et al. |
| 2020/0179929 A1 | 6/2020 | Sherman et al. |
| 2020/0182784 A1 | 6/2020 | Nagai et al. |
| 2020/0222894 A1 | 7/2020 | Bosy et al. |
| 2020/0225143 A1 | 7/2020 | Mach et al. |
| 2020/0278286 A1 | 9/2020 | Vacca |
| 2020/0309670 A1 | 10/2020 | Du et al. |
| 2021/0231642 A1 | 7/2021 | Wilson et al. |
| 2021/0283601 A1 | 9/2021 | Sun et al. |
| 2021/0283607 A1 | 9/2021 | Augustsson et al. |
| 2022/0018827 A1 | 1/2022 | Samproni et al. |
| 2022/0091068 A1 | 3/2022 | Irving et al. |
| 2022/0113291 A1 | 4/2022 | Bosy et al. |
| 2022/0113297 A1 | 4/2022 | Bosy et al. |
| 2022/0143611 A1 | 5/2022 | Paulicka et al. |
| 2023/0194555 A1 | 6/2023 | Dobromyslin et al. |
| 2024/0044795 A1 | 2/2024 | Vo et al. |

FOREIGN PATENT DOCUMENTS

| | | |
|---|---|---|
| CN | 1200657 A | 12/1998 |
| CN | 1502068 A | 6/2004 |
| CN | 1906485 A | 1/2007 |
| CN | 101060898 A | 10/2007 |
| CN | 102257418 A | 11/2011 |
| CN | 104107561 A | 10/2014 |
| DE | 102004013960 A1 | 8/2005 |
| EP | 0597577 A1 | 5/1994 |
| EP | 0795129 A1 | 9/1997 |
| EP | 3245001 A1 | 11/2017 |
| JP | 2000-199744 A | 7/2000 |
| JP | 2001-258868 A | 9/2001 |
| JP | 2008-051824 A | 3/2008 |
| JP | 2008-134063 A | 6/2008 |
| WO | 96/17243 A1 | 6/1996 |
| WO | 97/15229 A1 | 5/1997 |
| WO | 2005/054811 A2 | 6/2005 |
| WO | 2005/089082 A2 | 9/2005 |
| WO | 2010/038230 A1 | 4/2010 |
| WO | 2010/123453 A1 | 10/2010 |
| WO | 2011/006525 A1 | 1/2011 |
| WO | 2013/177560 A1 | 11/2013 |
| WO | 2014/133451 A1 | 9/2014 |
| WO | 2014/178782 A1 | 11/2014 |
| WO | 2016/115014 A1 | 7/2016 |
| WO | 2018065626 A1 | 4/2018 |
| WO | 2020/033192 A1 | 2/2020 |
| WO | 2020/118018 A1 | 6/2020 |
| WO | 2020/118021 A1 | 6/2020 |
| WO | 2020/190462 A1 | 9/2020 |
| WO | 2022/031459 A1 | 2/2022 |
| WO | 2024/005867 A1 | 1/2024 |

OTHER PUBLICATIONS

Cao et al., "A Microfluidic Device with Integrated Sonication and Immunoprecipitation for Sensitive Epigenetic Assays", American Chemical Society, vol. 88, 2016, pp. 1965-1972.

Claims for European Patent Application No. 24179423.9 accessed on Sep. 9, 2025 (3 pages).

Decision to Grant received for European Patent Application No. 16703385.1, mailed on May 16, 2024, 2 pages.

Duck et al., "Frequency bands for ultrasound, suitable for the consideration of its health effects", The Journal of the Acoustical Society of America, vol. 144, No. 4, Oct. 2018, pp. 2490-2500.

Final Office Action for U.S. Appl. No. 14/992,284, issued Aug. 12, 2022, (12 pages).

Final Office Action, U.S. Appl. No. 14/992,284, filed Dec. 22, 2017, dated Apr. 10, 2018, 10 pages.

Guhr et al., "Novel Sensor combining impedance spectroscopy and surface acoustic waves to detect blood coagulation time and hematocrit value", IEEE Sensors Proceedings, Limerick, Ireland, 2011, 4 pages.

Khanna et al., "Nanocrystalline diamond microspikes increase the efficiency of ultrasonic cell lysis in a microfluidic lab-on-a-chip", Diamond & Related Materials, vol. 18, 2009, pp. 606-610.

Lakamper et al., "Direct 2D measurement of time-averaged forces and pressure amplitudes in acoustophoretic devices using optical trapping", The Royal Society of Chemistry, Lab on a Chip, vol. 15, 2015, pp. 290-300.

Lenshof et al., "Acoustofluidics 8: Applications of acoustophoresis in continuous flow microsystems", The Royal Society of Chemistry, Lab Chip, vol. 12, 2012, pp. 1210-1223.

Non-Final Office Action for U.S. Appl. No. 14/992,284, dated Apr. 5, 2022, (12 pages).

Non-Final office action received for U.S. Appl. No. 16/336,832, mailed on Oct. 1, 2021, 21 pages.

Non-Final Office Action, U.S. Appl. No. 14/992,284, filed Dec. 22, 2017, 9 pages.

Notice of Acceptance for Patent Application dated Dec. 14, 2021, for Australian Application No. 2020204565 (3 pages).

Notice of Allowance in U.S. Appl. No. 15/791,734 dated Apr. 24, 2024, 10 pages.

Office Action received for Chinese Patent Application No. 201980077921.9, mailed on Aug. 19, 2024, 14 pages (9 pages of English Translation and 5 pages of Original Document).

Office Action received for Chinese Patent Application No. 201980077921.9, mailed on Jan. 4, 2025, 14 pages (9 pages of English Translation and 5 pages of Original Document).

Office Action received for Chinese Patent Application No. 202210640852.1, mailed on Apr. 23, 2025, 32 pages (17 pages of English Translation and 15 pages of Original document).

Office Action received for European Patent Application No. 16703385.1, mailed on Jun. 25, 2019, 5 pages.

Office Action received for European Patent Application No. 16703385.1, mailed on Mar. 11, 2021, 4 pages.

Office Action received for European Patent Application No. 23164469.1, mailed on Aug. 20, 2025, 6 pages.

Ozcelik et al., "An Acoustofluidic Micromixer via Bubble Inception and Cavitation from Microchannel Sidewalls", American Chemical Society, vol. 86, 2014, pp. 5083-5088.

Seo et al., "Ultrasonic flow through filtration of microparticles in a microfluidic channel using frequency sweep technique", Journal of Mechanical Science and Technology, vol. 27, No. 3, 2013, pp. 825-830.

Sinclair et al., "Design, construction, characterization, and application of a hyperspectral microarray scanner", Applied Optics, vol. 43, No. 10, Apr. 1, 2004, pp. 2079-2088.

Third Party Observations received for European Patent Application No. 24179423.9, mailed on Aug. 28, 2025, 4 pages.

Trafton, Anne, "Sorting Cells with Sound Waves," Massachusetts Institute of Technology, MIT News, Available online at: <https://news.mit.edu/2014/sorting-cancer-cells-with-sound-0825#:?:text=Caption%3A-This%20microfluidic%20device%20uses%20sound%20waves%20to%20sorts%20cells%20as,channel%2C%20from%20left%20to%20right.&text=Researchers%20from%20MIT%2C%20Pennsylvania%20State,flow%20through%20a%20tiny%20channel>, 2014, 2 pages.

Wang et al., "Cell lysis via acoustically oscillating sharp edges", Lab Chip, vol. 19, No. 24, Dec. 21, 2019, 12 pages.

Non-Final Office Action in U.S. Appl. No. 17/560,828 dated Jul. 19, 2023 (11 pages).

Non-Final Rejection issued on Feb. 15, 2018 in the U.S. pub. 20180052147; 9 pgs.

Petersson, et al., "Separation of lipids from blood utilizing ultrasonic standing waves in microfluidic channels," Analyst, 129:938-943 (2004).

Second Office issued in corresponding Chinese application No. 201680005603.8, dated Mar. 5, 2020 (No. of pp. 8), and English summary thereof (No. of pp. 3).

Summons to attend oral proceedings pursuant to Rule 115(1) EPC in EP Application No. 16703385.1 dated Nov. 3, 2023, 6 pages.

(56) References Cited

OTHER PUBLICATIONS

Tao Dong et al. Review: Recent Developments in Optical Detection Technologies in Lab-on-a-Chip Devices for Biosensing Applications, Sensors, 2014, 14, 15458-15479; doi: 10.3390/s140815458.
Third Office Action for Chinese patent application No. 2016800056038, issued Oct. 30, 2020, with English translation, (14 pages).
Vitali et al., "Differential impedance spectra analysis reveals optimal actuation frequency in bulk mode acoustophoresis," Scientific Reports 9:19081 (2019), 30 pages.
Yasuda et al Article "Non-destructive, non-contact handling method for biomaterials in micro-chamber by ultrasound", Sensors and Actuators B 64 (2000), pp. 128-135.
Search Report for related LU Application No. 103236 dated Jun. 27, 2024 (8 pgs.).
Extended European Search Report received for European Patent Application No. 24218550.2, mailed on Jan. 16, 2025, 9 pages.
Peterson et al., "Development of an Ultrasonic Blood Cell Separator", Proceedings of the Annual Conference of the IEEE/Engineering in Medicine and Biology Society. Fort Worth, Nov. 7-10, 1986; [proceedings of the Annual International Conference of the Engineering in Medicine and Biology Society], New York, IEEE, US, XP000938696, vol. Conf. 8, 1986, pp. 154-156.
Petersson et al., "Acoustofluidic hematocrit determination", Analytica Chimica Acta, XP085323313, ISSN: 0003-2670, vol. 1000, Nov. 22, 2017 (Nov. 22, 2017), pp. 199-204.
Adams et al., "High-throughput, temperature-controlled microchannel acoustophoresis device made with rapid prototyping," J. Micromech. Microeng., 22:1-8 (2012).
Additional English machine translation of AI .(JP 2000-199744 A), as supplied by Patent Translate (description only).
Australian Examination Report issued in Australian Patent Application No. 2018236886, mailed Jul. 8, 2019, 3 pages.
Canadian Office Action for Canadian Patent Application No. 2,972,848 dated Oct. 22, 2018, 4 pages.
Chen et al., "Standing surface acoustic wave (SSAW)-based microfluidic cytometer," Lab Chip, 14:916-923 (2014).
Chinese Office Action issued in corresponding Chinese application No. 2016800056038, dated Jul. 8, 2019, and English translation thereof, 12 pages.
Christopher-John L Farrell et al.: "Serum indices: managing assay interference", Annals of Clinical Biochemistry., vol. 53, No. 5, Sep. 1, 2016, pp. 527-538, XP055652917, GB ISSN: 0004-5632, DOI: 10.1177/0004563216643557.
Chwee Tack Lim et al. Microfluidic Devices for Blood Fractionation, Micromachines 2011, 2, 319-343; doi: 10.3390/mi2030319.
Communication pursuant to Articie 94(3) EPC for European patent application No. 16703385.1, issued Feb. 8, 2023, (5 pages).
Communication pursuant to Article 94(3) EPC issued in European Patent Application No. 16 703 385.1, mailed Jun. 25, 2019, 5 pages.
Communication pursuant to Rule 114(2) EPC for European Application No. 16703385.1, mailed Dec. 8, 2022, (21 pages).
De Sarabia et al., "Application of high-power ultrasound to enhance fluid/solid particle separation processes," Ultrasonics, 38:642-646 (2000).
Elodie Sollier et al. Micro-scale blood plasma separation: from acoustophoresis to egg-beaters, Lab on a Chip, 2013, 13, Issue 17, 1-24; doi: 10.1039/c3lc50432h.
English machine translation of AI (JP 2000-199744 A), as supplied by Espacenet.
Examination Report issued in corresponding Canadian application No. 2,972,848, 5 pages.
Examination Report No. 1 in AU Application No. 2022201391 dated Apr. 24, 2023 (4 pages).
Examination Report No. 2 for Australian Application No. 2022201391 dated Jan. 29, 2024, 5 pages.
Examiner Requisition for Canadian patent application No. 2,972,848, issued Apr. 19, 2021, (9 pages).
Examiner Requisition for Canadian patent application No. 2,972,848, issued Nov. 3, 2021, (14 pages).

Extended European Search Report in EP Application No. 23164469.1 dated Jun. 12, 2023 (11 pages).
Extended European Search Report received for European Patent Application No. 24179423.9, mailed on Sep. 20, 2024, 10 pages.
Farkas et al. Thermochimica Acta, 2003, 404, pp. 141-148.
Fifth Office Action for Chinese patent applicatian No. 2016800056038, issued Dec. 9, 2021, with English Summary, (14 pages).
Final Office Action for U.S. Appl. No. 14/992,284, issued Jul. 16, 2021, (18 pages).
Final Office Action for U.S. Appl. No. 15/791,734, issued Dec. 28, 2020, (24 pages).
Final Office Action for U.S. Appl. No. 15/791,734, issued Dec. 30, 2022, (30 pages).
Final Office Action for U.S. Appl. No. 15/791,734, issued Mar. 17, 2022, (15 pages).
Final Office Action for U.S. Appl. No. 17/560,828, issued Dec. 30, 2022, (13 pages).
Final Rejection issued on Sep. 5, 2018 in U.S. Publication No. 2018/0052147, 14 pages.
Fourth Office Action for Chinese patent application No. 2016800056038, issued Jul. 20, 2021, (17 pages).
Gossett et al. Label-free cell separation and sorting in microfluidic systems, Anal Bioanal Chem (2010) 397:3249-3267, DOI 10.1007/s00216-010-3721-9.
Henkelman et al. Materials Science and Engineering C 29 (2009) 1650-1654.
Hun Lee et al. Review: Various On-Chip Sensors with Microfluidics for Biological Applications Sensors 2014, 14, 17008-17036; doi:10.3390/s140917008.
International Preliminary Report on Patentability for International Patent Application No. PCT/US2019/054289, issued Apr. 15, 2021, 8 pages.
International Preliminary Report on Patentability, dated Jul. 18, 2017, International Application No. PCT/US2016/012811, pp. 1-6.
International Search Report and Written Opinion for International Application No. PCT/US2016/012811, dated Apr. 15, 2016, 11 pages.
Japanese Office Action, Application No. 2017-534914, dated Jul. 9, 2018, 9 pages (includes both English and Japanese language versions).
Japanese Ofice Action, Japanese Patent Application No. 2017-534914, mailed Mar. 6, 2019, 2 pages (translation included, 3 pages).
Jonsson et al., "Particle Separation Using Ultrasound Can Radically Reduce Embolic Load to Brain After Cardiac Surgery," Ann Thorac Surg., 78:1572-1577 (2004).
Laurell, "Chip integrated strategies for acoustic separation and manipulation of cells and particles," Chem. Soc. Rev., 36:493-506 (2007).
Lenshof et al. "Acoustic Whole Blood Plasmapheresis Chip for Prostate Specific Antigen Microarray Diagnostic". Anal. Chem. 2009, 81, 6030-6037.
Manneberg, "Flow-free Transport of Cells in Microchannels by Frequency-modulated Ultrasound", The Royal Society of Chemistry, 2009, vol. 9, pp. 833-837.
Nam, J et al. "Separation of platelets from whole blood using standing surface acoustic waves in a microchannel," Lab Chip, 2011, 11, 3361-3364. (Year: 2011).
Non-Final Office Action and Examiner Interview Summary in U.S. Appl. No. 15/791,734 dated Oct. 2, 2023 (19 pages).
Non-Final Office Action for U.S. Appl. No. 14/992,284, issued Feb. 23, 2021, (12 pages).
Non-Final Office Action for U.S. Appl. No. 15/791,734, issued Jun. 20, 2022, (19 pages).
Non-Final Office Action for U.S. Appl. No. 15/791,734, issued Jun. 9, 2021, (25 pages).
Non-Final Office Action for U.S. Appl. No. 16/591,413, issued May 19, 2021, (19 pages).
Non-Final Office Action for U.S. Appl. No. 17/560,828, issued Aug. 4, 2022, (7 pages).

ACOUSTIC SEPARATION OF A TEST SAMPLE

TECHNICAL FIELD

This specification relates generally to diagnostic testing and devices for use during diagnostic testing.

BACKGROUND

A test sample may include particles and liquid. For example, a test sample may be blood or a blood product that includes plasma and red blood cells.

Acoustic waves can be applied to the test sample to separate the particles from liquid. The acoustic waves create one or more pressure nodes within the test sample, which correspond to regions of maximum and minimum pressure in the test sample. The particles move to the locations of minimum pressure, thereby concentrating the particles in some regions of the test sample and leaving other regions of the test sample completely or substantially devoid of particles. Systems that employ acoustic waves to separate particles from liquid use a fixed drive routine to create standing acoustic waves. Such drive routines are used to control an acoustic transducer to produce acoustic waves having parameters, such as amplitude, frequency, and/or duration, that do not change.

Acoustic waves created using fixed drive routines may not always be sufficient to separate particles from liquid. More specifically, as the percentage by volume of particles in a test sample increases, it can become more difficult to separate the particles from the liquid using acoustic waves created using fixed drive routines. For example, as the hematocrit of a blood sample increases above 50% or 60%, some systems may be unable to sufficiently separate red blood cells from plasma using fixed drive routines, since those fixed drive routines may not produce acoustic waves having sufficient amplitudes, durations, and/or frequencies to produce the separation. Simply modulating these parameters of a drive routine can cause problems. For example, increasing the voltage in a drive routine, which is used to control the amplitude of the acoustic waves, may improve separation, but can also damage the test sample.

SUMMARY

An example system includes a detector configured to detect a value that is based on a hematocrit of a test sample containing plasma and red blood cells, a fluidic channel configured to hold the test sample, and an acoustic transducer configured to apply acoustic waves to the fluidic channel to separate the plasma from the red blood cells in the fluidic channel. The acoustic waves have at least one of an amplitude, a frequency, or a duration that is based on the value. The example system may include one or more of the following features, either alone or in combination.

The system may include an optical detector configured to perform optical detection on the plasma separated in the fluidic channel, and a control system configured to determine hemolysis in the test sample based on a result of the optical detection. The value that is based on the hematocrit may be fluid electrical resistance. The fluid electrical resistance may vary with the hematocrit. The fluid electrical resistance may correspond to a voltage difference between two locations in the test sample. All of the amplitude, the frequency, and the duration of the acoustic waves may be based on the fluid electrical resistance.

Separating the plasma from the red blood cells in the fluidic channel may include forming a region of plasma in a center of the fluidic channel. Separating the plasma from the red blood cells in the fluidic channel may include forming a region of red blood cells in a center of the fluidic channel.

The control system may be configured to control the acoustic transducer based on the value to produce acoustic waves having the amplitude. The detector may be configured to detect changes over time in the value. The control system may be configured to control the acoustic transducer to adjust at least one of the amplitude, the frequency, or the duration of the acoustic waves applied to the fluidic channel based on a detected change to the value over time.

The control system may be configured to control the acoustic transducer based on the value to apply the acoustic waves to the fluidic channel. Controlling the acoustic transducer based on the value may include selecting a drive routine from among multiple drive routines stored in memory, with each drive routine specifying, for a corresponding value based on the hematocrit, a voltage corresponding to an amplitude of acoustic waves to be produced by the acoustic transducer, a frequency of acoustic waves to be produced by the acoustic transducer, and the duration of acoustic waves to be applied by the acoustic transducer. The acoustic transducer may be controlled in accordance with the drive routine that was selected.

The system may include memory storing a look-up table (LUT). The LUT may store multiple voltages, with each voltage corresponding to an amplitude of acoustic waves for a specified value; multiple frequencies, with each frequency corresponding to a frequency of acoustic waves for a specified value; and multiple durations, with each duration corresponding to a duration of acoustic waves to be applied for a specified value. The control system may be configured to control the acoustic transducer by selecting a voltage from the LUT based on the value, selecting a frequency from the LUT based on the value, selecting a duration from the LUT based on the value, and controlling the acoustic transducer based on the voltage selected, the frequency selected, and the duration selected.

An example method includes determining a value based on a hematocrit of a test sample that includes of plasma and red blood cells; applying acoustic waves to a fluidic channel containing the test sample to separate the plasma from the red blood cells, with at least one of an amplitude, a frequency, or a duration of the acoustic waves applied to the fluidic channel being based on the value; performing optical detection on the plasma; and determining hemolysis of the test sample based on a result of the optical detection. The example method may include one or more of the following features, either alone or in combination.

The amplitude, the frequency, and the duration of the acoustic waves applied to the fluidic channel may all be based on the value. The acoustic waves may be applied by an acoustic transducer. Controlling the amplitude may include applying a voltage to the acoustic transducer. Determining the value may include measuring a voltage difference between two locations in the test sample. The voltage difference may correspond to a fluid electrical resistance of the test sample. The fluid electrical resistance may vary proportionally with the hematocrit.

Separating the plasma from the red blood cells in the fluidic channel may include forming a region of plasma in a center of the fluidic channel. Separating the plasma from the red blood cells in the fluidic channel may include forming a region of red blood cells in a center of the fluidic channel.

Detecting the value of the test sample may be performed over time. The method may include changing at least one of the amplitude, the frequency, or the duration of the acoustic waves applied to the fluidic channel based on a detected change to the value over time.

An example system includes a detector configured to detect a value that is based on a hematocrit of a test sample comprised of plasma and red blood cells; a fluidic channel configured to hold the test sample; an acoustic transducer configured to apply acoustic waves to the fluidic channel to separate the plasma from the red blood cells in the fluidic channel; and a control system configured to control the acoustic transducer to produce acoustic waves that sweep over a range of frequencies. The range of frequencies is based on the hematocrit. The example system may include one or more of the following features, either alone or in combination.

The system may include an optical detector configured to perform optical detection on the plasma separated in the fluidic channel, and a control system configured to determine hemolysis in the test sample based on a result of the optical detection. The range of frequencies may be a first range of frequencies. The detector may be configured to detect changes in the value over time. The control system may be configured to control the acoustic transducer to produce acoustic waves that sweep over a second range of frequencies that is different from the first range of frequencies. The second range of frequencies may be based on a detected change to the value over time. The range of frequencies may include frequencies greater than 1.85 megahertz (MHz).

Any two or more of the features described in this specification, including in this summary section, may be combined to form implementations not specifically described in this specification.

At least part of the devices, systems, and processes described in this specification may be configured or controlled by executing, on one or more processing devices, instructions that are stored on one or more non-transitory machine-readable storage media. Examples of non-transitory machine-readable storage media include read-only memory, an optical disk drive, memory disk drive, and random access memory. At least part of the devices, systems, and processes described in this specification may be configured or controlled using a computing system comprised of one or more processing devices and memory storing instructions that are executable by the one or more processing devices to perform various control operations. The devices, systems, and processes described in this specification may be configured, for example, through design, construction, composition, arrangement, placement, programming, operation, activation, deactivation, and/or control.

The details of one or more implementations are set forth in the accompanying drawings and the following description. Other features and advantages will be apparent from the description and drawings, and from the claims.

DESCRIPTION OF THE DRAWINGS

Like reference numerals in different figures indicate like elements.

DETAILED DESCRIPTION

Hemolysis is the rupture or destruction of red blood cells in a biological test sample ("test sample"), such as blood or a blood product. The example systems and processes presented herein are described in the context of determining hemolysis in a blood sample optically. However, the example systems and processes may also be used to determine the presence, in a test sample, of analytes such as, but not limited to, glucose, lactate, sodium, potassium, chloride, phosphate, total protein, alanine aminotransferase, aspartate aminotransferase, alkaline phosphatase, lactate dehydrogenase, albumin, total globulin, hemoglobin, troponin I, cholesterol, coagulation factors, circulating tumor cells (CTC), and/or cell fractions.

A test sample contains liquid, such as plasma, in addition to particles, such as the red blood cells. To determine hemolysis in the test sample using optical detection, acoustic waves are applied to separate the plasma from the red blood cells so that an optical detector, which may include a camera, can capture an image of a resulting cell-free plasma region in the test sample.

Optical detection may require that the cell-free plasma region have a sufficiently large size so that the camera can capture an image that is large enough to analyze. In some examples, to perform optical detection on the cell-free plasma region, the cell-free plasma may be required to have a minimum width of 70 microns (μm) (referred to as "separation width" or "plasma width") and a minimum area corresponding to 2000 pixels of the camera. The examples presented herein use these values. However, the values of the separation width and area may differ for different cameras and test configurations. For example, in some implementations, to perform optical detection on a cell-free plasma region, the cell-free plasma may be required to have a minimum width of 1 μm to 10 μm and a minimum area corresponding to one pixel to 1000 pixels of the camera used in the optical detector.

Figure 1A:
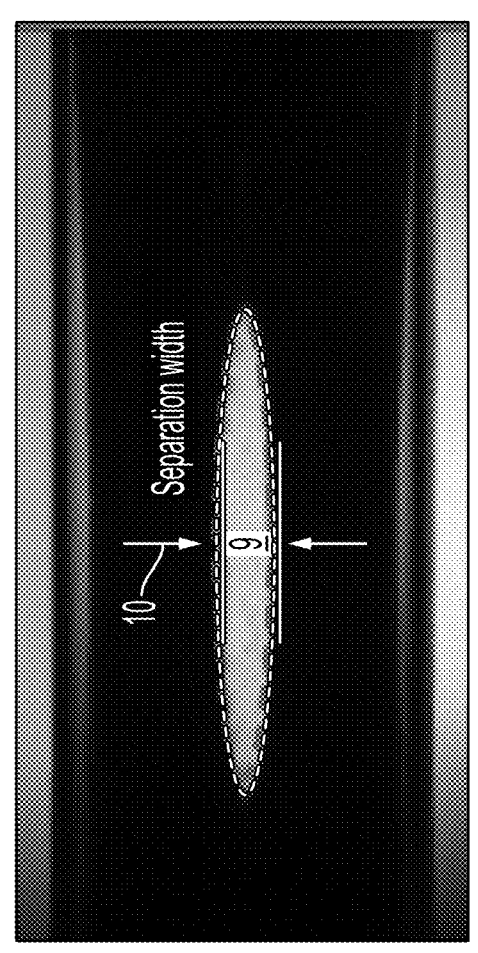
FIG. 1A is a diagram showing an example microchannel containing a test sample, having a small separated cell-free plasma region in its middle.

Hematocrit is the volume percentage of red blood cells in a test sample. Test samples having a relatively high hematocrit, such as a hematocrit of 50% or 60% or greater (meaning that 50% or 60% or greater of the test sample volume is red blood cells), can be more difficult to acoustically separate into red blood cell regions and cell-free plasma regions than test samples having a relatively low hematocrit, such as less than 50%. This is because, in test samples having relatively high hematocrit, higher-energy, longer duration, and/or different frequency acoustic waves may be required to produce a cell-free plasma region having a sufficiently large size. Fixed drive routines, which were described previously, may cause an acoustic transducer to produce acoustic waves having a frequency, amplitude, and/or duration that is/are inadequate to produce a cell-free plasma region with a sufficient size for analysis. For example, FIG. 1A shows a cell-free plasma region 9 produced by an acoustic transducer using a fixed drive routine, which has a separation width 10 that is insufficiently large in size for optical detection for at least some optical detectors.

Accordingly, the example systems and processes described herein are configured (i) to determine a value that corresponds to—for example, that varies with, is proportional to, and/or is based on—the hematocrit of a test sample and (ii) to generate acoustic waves having an amplitude, a frequency, and/or a duration that is/are tailored to that value. In this example, the value is the fluid electrical resistance of the test sample. The fluid electrical resistance is a measure of a fluid's ability to oppose electric current. The fluid electrical resistance is measured in ohms, but since electrical current in the test sample, if any, is constant, the fluid electrical resistance and voltage difference across two locations of the test sample are directly proportional. Accordingly, the fluid electrical resistance of the test sample is reported as a voltage measurement.

Figure 1B:
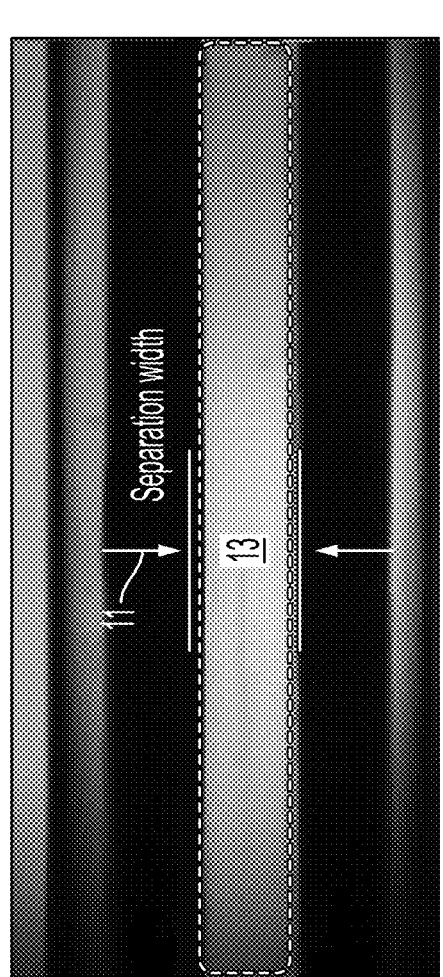
FIG. 1B is a diagram showing an example microchannel containing a test sample, with a large separated cell-free plasma region in its middle.

In some implementations, the acoustic waves that are generated based on the value corresponding to the hematocrit are capable of separating red blood cells well enough to produce a cell-free plasma region having a size that is sufficient for optical detection without damaging the test sample. The example of FIG. 1B, which is of the same sample as that shown in FIG. 1A, shows a cell-free plasma region 13 generated using that systems and processes described herein, which has a sufficiently large size—here, separation width 11—for optical detection. As shown, the separation width 11 and the area of cell-free plasma region 13 are both greater in the example of FIG. 1B than in the example of FIG. 1A because the amplitude, frequency, and/or duration of the acoustic waves that were used to generate cell-free plasma region 13 were tailored to improve the separation for the test sample.

The example systems may also be configured to continuously, periodically, or intermittently monitor the fluid electrical resistance of the test sample to infer changes in the hematocrit over time. The systems may then make any adjustments to the amplitude, frequency, and/or duration of the acoustic waves that may be necessary to accommodate the inferred changes in the hematocrit. For example, the fluid electrical resistance can be monitored at least once for each sample so that values for the amplitude, frequency, and/or duration can be selected for optimal or improved separation.

In some implementations, the example systems are configured to vary one or more of the amplitude, frequency, and/or duration of the acoustic waves, while keeping the other(s) constant. For example, the systems may sweep the frequency of the acoustic waves across a range of frequencies, while keeping the amplitude and duration of the acoustic waves constant. The frequency sweep may be tailored to a hematocrit of the test sample as inferred from a measured fluid electrical resistance of the test sample, thereby producing, in some cases, a cell-free plasma region having a sufficiently large size for optical detection without damaging the test sample.

The example systems may be implemented on a clinical analyzer that is usable in a point-of-care (POC) setting such as an emergency room. Example clinical analyzers used to implement the example systems and processes may include blood gas devices configured to process blood samples with a wide range of electrolytes, protein, osmolarity, red blood cell concentrations, and other blood components.

Figure 2:
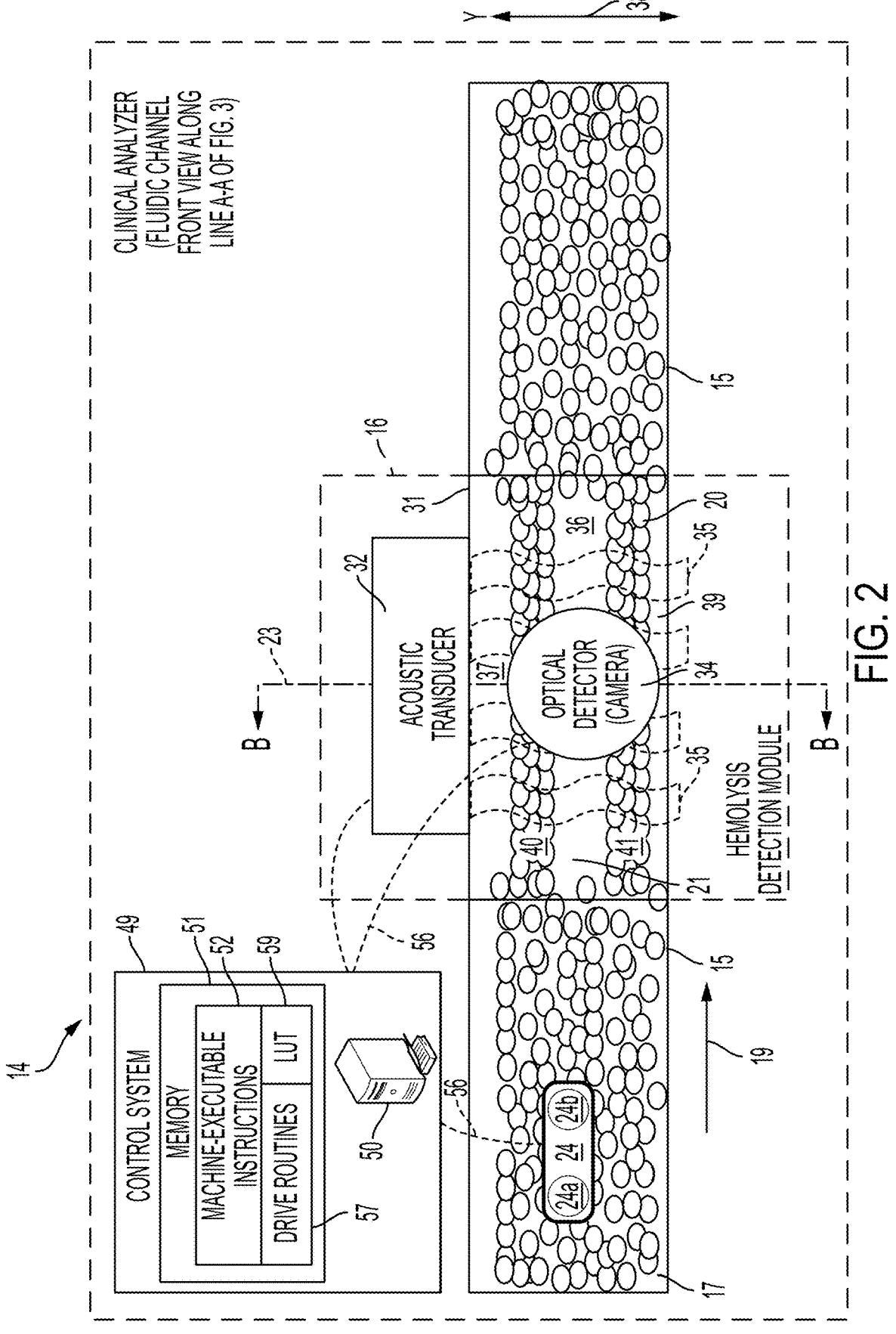
FIG. 2 is a block diagram showing a front view of example components included in an example clinical analyzer, which was taken along line A-A of FIG. 3.
Figure 3:
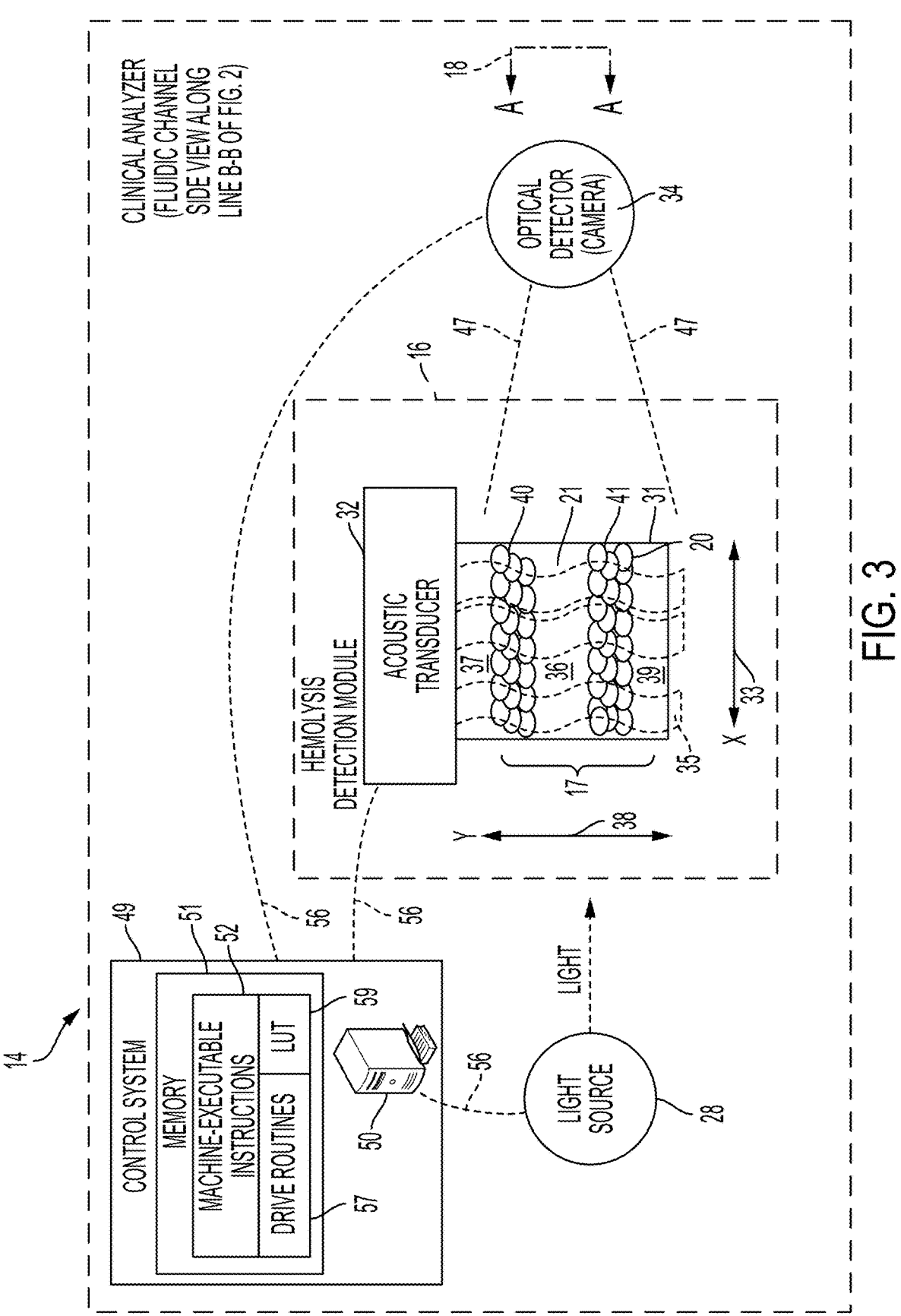
FIG. 3 is a block diagram showing a cross-sectional side view of example components included in an example clinical analyzer, which was taken along line B-B of FIG. 2.

FIG. 2 is a front view of some of the components included in an example clinical analyzer 14 (e.g., a "system") on which the processes described herein may be implemented. FIG. 3 is a cross-sectional side view of the same components as FIG. 2. The view in FIG. 2 is taken along line A-A 18 of FIG. 3 and the view of FIG. 3 is taken along line B-B 23 of FIG. 2.

Referring to FIG. 2, clinical analyzer 14 includes a fluid line 15 separated from a hemolysis detection module ("module") 16, which is described below. In FIG. 3, fluid line 15 extends into and out of the page and, therefore, is not shown. Fluid line 15 may be made of plastic, glass, or other transparent material, and may include a tube or multiple interconnected tubes configured to transport a test sample 17. Fluid line 15 may have a circular cross-section, a rectangular cross-section, or any other shape that allows test sample 17 to flow through the fluid line. In this example, test sample 17 flows in the direction of arrow 19. In some examples, the width or diameter of the fluid line may be in the range of about 50 μm to 1.5 millimeters (mm).

An example of test sample 17 includes blood, such as whole blood, or a blood product. The test sample is comprised of particles such as red blood cells 20 and liquid such as cell-free plasma 21. The test sample flows from an input location (not shown) through fluid line 15 to, and through, a test location where hemolysis module 16 resides. Positive or negative pressure applied to the fluid line may cause the fluid flow.

Clinical analyzer 14 also includes a fluid detector 24 that is upstream in the fluid flow path (the direction of which is shown by arrow 19 as noted) from module 16. In some implementations, fluid detector 24 may be downstream of module 16. In this example, fluid detector 24 includes electrodes or probes 24a, 24b configured to measure voltages at different locations of test sample 17 and to determine a voltage difference based on those measurements. The voltage difference obtained by fluid detector 24 is proportional to the fluid electrical resistance of the test sample. To make the voltage measurements, the electrodes or probes 24a, 24b contact the test sample. To make this contact, in an example, fluid detector 24 may be located within, or be part of, fluid line 15. In another example, fluid detector 24 may be located outside of fluid line 15 but have probes 24a, 24b that extend into the interior of fluid line 15. In some implementations, fluid detector 24 may be a mechanical device configured to detect changes in pressure in the fluid flow that correspond to differences in hematocrit.

The fluid electrical resistance of the test sample corresponds to—for example, varies with, is proportional to, and/or is based on—the hematocrit and other constituents of the test sample. More specifically, as the hematocrit increases, the fluid electrical resistance increases and as the hematocrit decreases, the fluid electrical resistance decreases.

Figure 4:
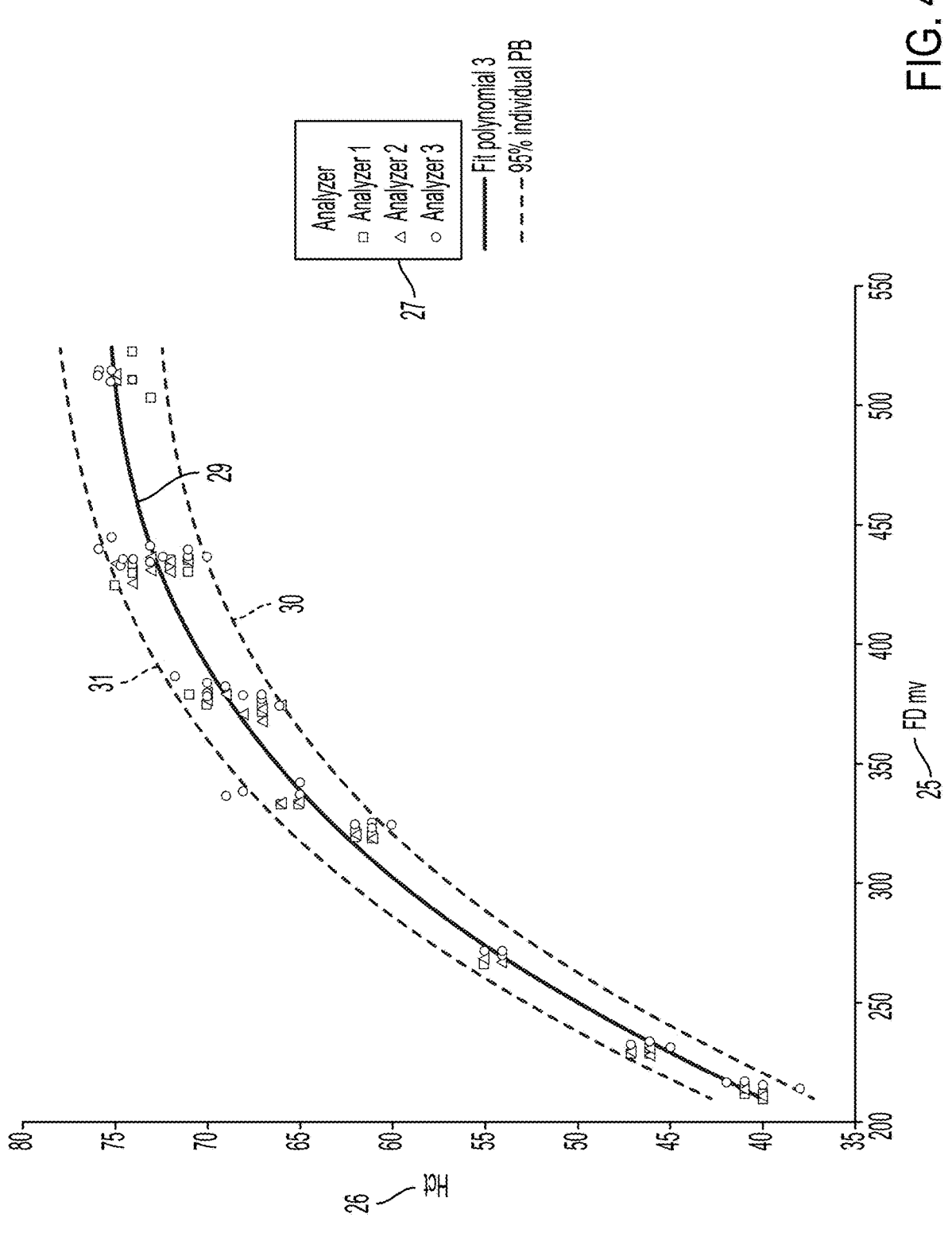
FIG. 4 is a graph showing the relationship between hematocrit and fluid electrical resistance in a test sample.

FIG. 4 shows the fluid electrical resistance 25 ("FD mv", where "FD" stand for fluid detector) of test samples having different hematocrit (Hct) levels 26. The fluid electrical resistance measurements in FIG. 4 were taken using three different clinical analyzers 27. A polynomial fit 29 to the measurements is also shown, along with curves 30, 31 containing 95% of the measured data. As shown in FIG. 4, the fluid electrical resistance 25 and the hematocrit 26 varies substantially linearly up until a hematocrit level of about 65%, whereafter the measurements plateau. Accordingly, in this example, over a hematocrit range of up to 65%, as the fluid electrical resistance increases, the hematocrit also increases substantially linearly. Consequently, a measured value of fluid electrical resistance in a test sample may be used as a proxy for a measurement of hematocrit in the test sample.

Referring to FIGS. 2 and 3, module 16 is located along the path of fluid line 15. In this example, module 16 is configured, and used, to perform hemolysis testing on test sample 17. However, in some implementations, module 16 may be configured and/or used to test for one or more analytes in the test sample such as those listed above. Module may be characterized as an acoustofluidic device (AFD) because module 16 performs testing using acoustic waves on a fluid. In some implementations, module 16 may perform testing while test sample is flowing. In some implementations, module 16 may perform testing after fluid flow has stopped, e.g., while the fluid is not flowing.

Module 16 includes a microchannel 31 to hold test sample 17 and an acoustic transducer 32 to apply acoustic waves to test sample 17 to separate the plasma from the red blood cells. In some implementations, module 16 also includes an optical detector 34 to perform optical detection on the resulting cell-free plasma region or the resulting particle region in the microchannel. In some implementations, optical detector 34 is external to module 16.

Microchannel 31 is a fluidic channel configured to fluidically connect along fluid line 15, thereby creating a fluid flow path that includes fluid line 15 and microchannel 31, through which the test sample flows. Microchannel 31 may be made of plastic, glass, or other transparent material. Microchannel 31 may have a circular cross-section, a rectangular cross-section, or any other shape that allows test sample to flow through the microchannel. In some implementations, microchannel 31 may have a width or diameter that matches the width or diameter of fluid line 15. In some implementations, microchannel 31 may have a larger or longer dimension in Y 38 (e.g., vertical) than in X 33 (e.g., horizontal). This configuration may facilitate separation of the red blood cells 20 from the plasma 21.

Acoustic transducer 32 may be a piezoelectric transducer. A piezoelectric transducer includes a device that sends electrical energy in the form of an alternating electric field to a piezoelectric crystal in the transducer causing the crystal to vibrate and to convert the electrical energy into sound waves. Acoustic transducer 32 may be configured to generate one or more different types of acoustic waves, such as ultrasonic waves, surface acoustic waves, or bulk acoustic waves. In some implementations, the acoustic waves may have frequencies in the range of kilohertz (KHz) to 2 gigahertz (GHz) or greater or less than these values.

In some implementations, acoustic transducer 32 may be arranged near to—for example, within single-digit millimeters of—microchannel 31 although not in contact with microchannel 31. In some implementations, acoustic transducer 32 may be in contact with microchannel 31. Contact between the acoustic transducer and the microchannel may be direct as shown or indirect, meaning that there may be one or more structures between the acoustic transducer and the microchannel.

Acoustic transducer 32 may be excited using excitation parameters to produce acoustic waves. A control system, such as control system 49 described below, may provide the excitation parameters to acoustic transducer 32, or generate control signals based on the excitation parameters, to cause the acoustic transducer to generate acoustic waves having a specified amplitude, frequency, and/or duration. These excitation parameters include voltage/amplitude, energy/frequency, and timing/duration. A magnitude of the voltage applied to the acoustic transducer corresponds to the amplitude of the acoustic waves produced by the acoustic transducer. For example, the greater the voltage that is applied to the acoustic transducer, the greater are the amplitudes of the acoustic waves generated by the acoustic transducer. The frequency is the frequency of acoustic waves to be produced by the acoustic transducer. The frequency may be based on electrical energy provided to the acoustic transducer. The excitation parameters may include the magnitude and frequency of this electrical energy. The duration is the length of time that the acoustic waves are applied to the acoustic transducer. For example, the duration specifies the amount of time that the electrical energy and voltage are to be applied to the acoustic transducer to effect to a predefined amount (e.g., an optimal) separation of plasma 21 and red blood cells 20.

Figure 5:
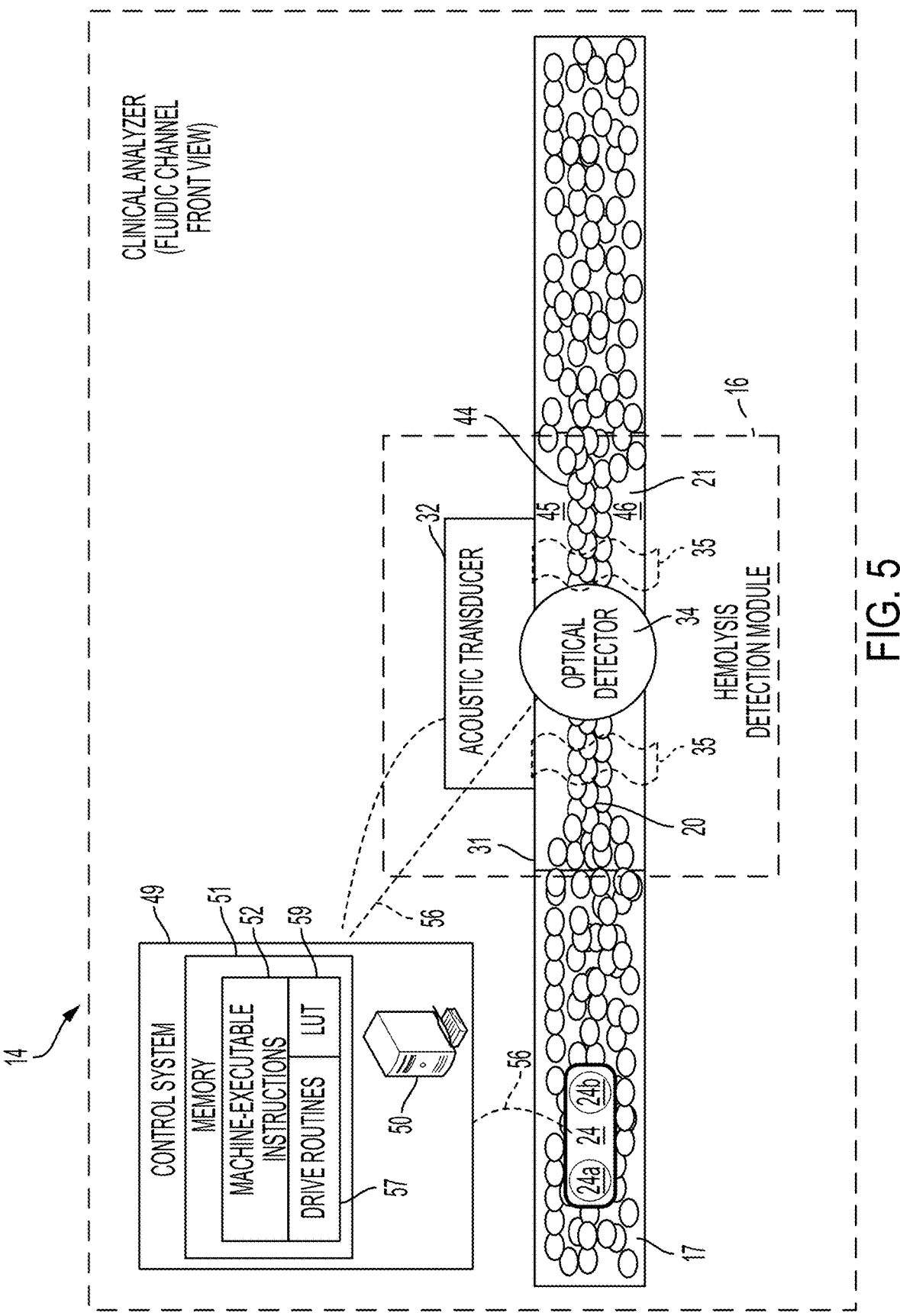
FIG. 5 is a block diagram of a front view of example components included in an example clinical analyzer, which is similar view to that of FIG. 2 but which includes a particle region at a center of the microchannel.

In the example of FIGS. 2 and 3, acoustic transducer 32 is configured and arranged to produce acoustic waves 35 that separate plasma 21 from red blood cells 20 in microchannel 31 to form a region 36 of cell-free plasma in a center of microchannel 31. In this example, the acoustic waves also form regions 37, 39 of cell-free plasma adjacent to one or more surfaces of microchannel 31. In some implementations, there may be more or fewer regions of cell-free plasma than those shown in FIGS. 2 and 3. In some implementations, regions 37, 39 may be absent, and the red blood cells may abut and physically contact one or more surfaces of microchannel 31. In some implementations, there may be a region 36 of cell-free plasma in a center of microchannel bounded by regions 40, 41 containing red blood cells, but with multiple additional regions of cell-free plasma and red blood cells between each region 40, 41 and a surface of microchannel 31. Referring to FIG. 5, in some implementations, acoustic transducer 32 is configured and arranged to produce acoustic waves that form a region 44 containing red blood cells in a center of microchannel 31, with regions 45, 46 of cell-free plasma on either or both side(s) of region 44. In some implementations, there may be multiple particle and cell-free plasma regions between region 44 and the surface of microchannel 31. U.S. Patent Publication No. 2016/0202237 (Zeng), which was published on Jul. 14, 2016, describes different types of plasma/particle separation that may be implemented using acoustic transducer 32. U.S. Patent Publication No. 2016/0202237 is incorporated herein by reference, particularly with respect to its description relating to cell/plasma separation.

Referring back to FIGS. 2 and 3, optical detector 34 is arranged to capture images of one or more cell-free plasma regions, such as region 36, or one or more particle regions such as region 44. The examples presented below have optical detector capturing an image of cell-free plasma region 36. In this example, optical detector 34 includes a camera having a pixelated images sensor configured to capture the images. In some implementations, optical detector is lined-up with—for example, along side of—microchannel 31 as shown in FIG. 3 to capture an image of microchannel within the camera's field-of-view 47. Generally, optical detector 34 may be placed at any location relative to the microchannel that enables the optical detector to capture an image of the entirety of the microchannel, an image of a cell-free plasma region 36, or an image of whatever region is of interest during testing at sufficient resolution to enable the image to be processed to determine hemolysis or to identify one or more analytes in the test sample, such as those described above. The distance between the microchannel and the camera can be within 0 mm to 500 mm, depending on the system design (e.g. using lens(es) in between the microchannel and the camera or not). A light source 28, such as one or more light-emitting diodes, outputs light to back-illuminate the microchannel, thereby making it easier for the camera to capture an image of all or part of the microchannel, including cell-free plasma region 36.

As noted, clinical analyzer 14 also includes control system 49. The control system may be an internal component of clinical analyzer 14 or the control system may be external to clinical analyzer 14. For example, the control system may be or include one or more computing devices that are local to (e.g., within the same room as) or remote from (e.g., in a different room from) the clinical analyzer.

In this example, control system 49 may include one or more processing devices 50 and memory 51 storing instructions 52 that are executable. The one or more processing devices 50 may execute instructions 52 to control, or to implement at least part of, processes 54 and 55 described below. Control system 49 is configured to communicate with fluid detector 24, light source 28, optical detector 34, and acoustic transducer 32. For example, control system 49 may be directly connected to fluid detector 24, light source 28, optical detector 34, and/or acoustic transducer 32 via one or more data buses or other wired connections. In some implementations, control system 49 may be connected to fluid detector 24, light source 28, optical detector 34, and/or acoustic transducer 32 over a wired or wireless computer network. Dashed lines 56 represent connections for communication.

Memory 51 also stores drive routines 57 and/or a look-up table (LUT) 59. Each drive routine 57 includes acoustic transducer excitation parameters tailored to a specific fluid electrical resistance. As noted above, example excitation parameters for acoustic transducer 32 include voltage/amplitude, electrical energy/frequency, and timing/duration. Accordingly, each drive routine may include one or more different numbers for each of these parameters. Each combination of these numbers has been previously determined based on testing performed using acoustic transducer 32 for different test samples having different fluid electrical resistances. Each combination of these numbers has been shown to cause acoustic transducer 32 to produce sufficiently large cell-free plasma regions for optical testing.

Each drive routine may include a voltage to be applied to an acoustic transducer to produce acoustic waves having an amplitude, which may be specified in the drive routine. Each drive routine may include a frequency of acoustic waves to be produced by the acoustic transducer, and an electrical energy used to produce that frequency. Each drive routine may include a duration that acoustic waves are to be applied by the acoustic transducer to produce a predefined separation width. The excitation parameters may be specific to the type of separation to be produced by the acoustic transducer. For example, drive routines that produce the type of blood cell/plasma separation shown in FIG. 2 may be different from drive routines that produce the type of blood cell/plasma separation shown in FIG. 5.

In an example, a fluid electrical resistance that is greater than a value of A (e.g., FD=450 mV, meaning that the fluid detector reports a value of 450 mV) is associated with a first drive routine; a fluid electrical resistance that is greater than a value of B (e.g., FD=400 mV) but less than or equal to a value of A is associated with a second drive routine; a fluid electrical resistance that is greater than a value of C (e.g., FD=300 mV) but less than or equal to a value of B is associated with a third drive routine; a fluid electrical resistance that is greater than a value of D (e.g., FD=200 mV) but less than or equal to a value of C is associated with a fourth drive routine; and so forth. Accordingly, if the fluid electrical resistance measured by fluid detector 24 is greater than A, then the control system may select the first drive routine and use it to drive acoustic transducer 32 to produce acoustic waves. If the fluid electrical resistance measured by fluid detector 24 is greater than B but less than or equal to A, then the control system may select the second drive routine and use it to drive acoustic transducer 32 to produce the acoustic waves; and so forth.

In some implementations, in lieu of drive routines, memory 51 may store LUT 59. LUT 59 may contain acoustic transducer excitation parameters for different values of fluid electrical resistance. For example, LUT 59 may contain multiple voltages and, in some examples amplitudes corresponding to the multiple voltages. Each voltage corresponds to a voltage to be applied to an acoustic transducer for a specified fluid electrical resistance to produce acoustic waves having an amplitude corresponding to that voltage. For example, LUT 59 may contain multiple frequencies and, in some examples, corresponding electrical energies to produce those frequencies. Each frequency may correspond to a frequency of acoustic waves to be produced by the acoustic transducer for a specified fluid electrical resistance. For example, LUT 59 may contain multiple durations. Each duration may correspond to a length of time that acoustic waves are to be applied by the acoustic transducer for a specified fluid electrical resistance to achieve a predefined separation width. Accordingly, in an example, if fluid detector 24 determines a fluid electrical resistance of a test sample, the control system may receive that determined fluid electrical resistance and use that determined fluid electrical resistance to access the LUT and to retrieve one or more or all excitation parameters for that fluid electrical resistance. The control system may use the excitation parameters to control acoustic transducer 32 to produce acoustic waves. As was the case above, the excitation parameters may be specific to the type of separation to be produced by acoustic transducer 32. For example, excitation parameters to produce the type of separation shown in FIG. 3 may be different from excitation parameters to produce the type of separation shown in FIG. 5.

Figure 6:
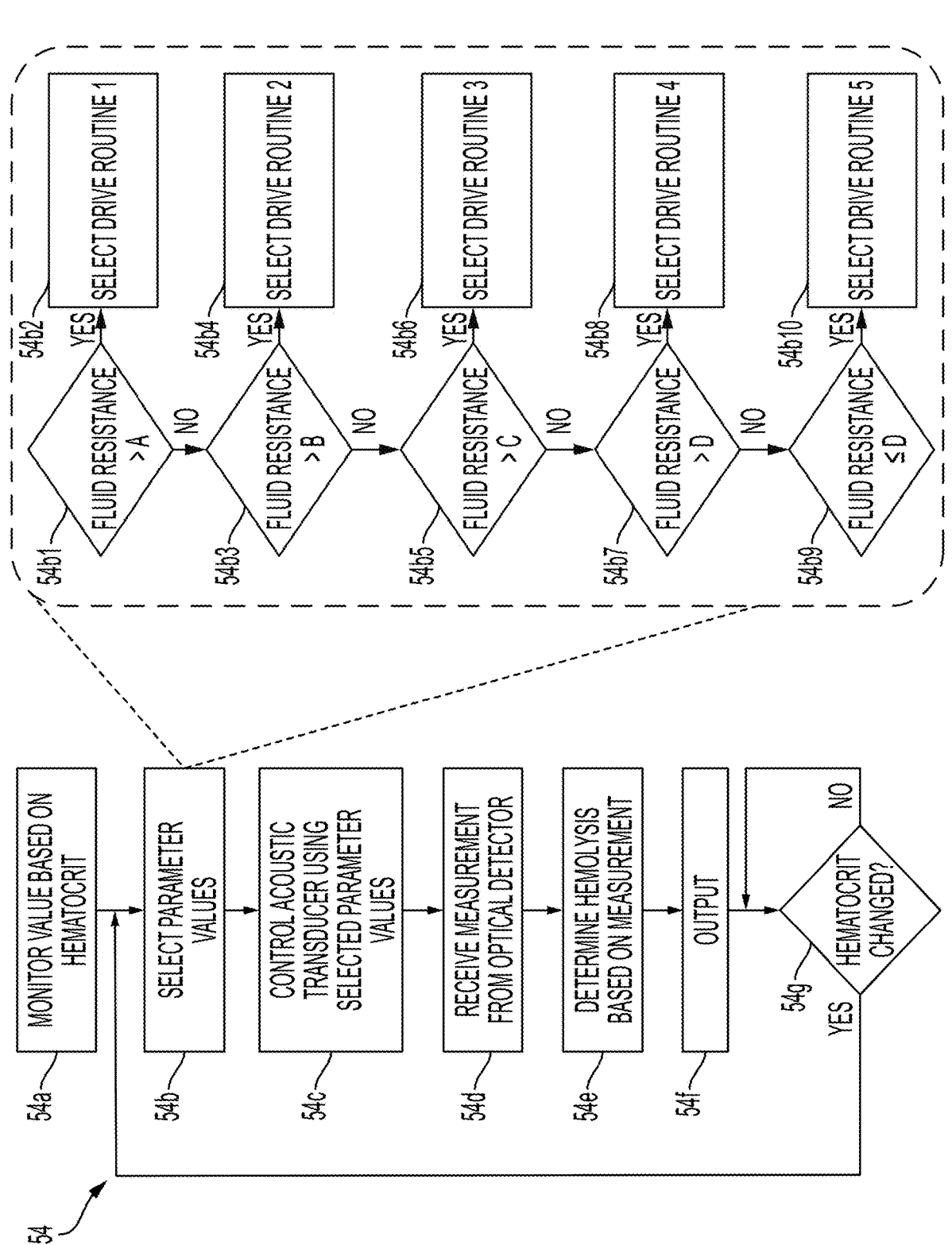
FIG. 6 is a flowchart showing operations included in an example process for controlling an acoustic transducer to produce acoustic waves that separate particles and liquid in a test sample.

FIG. 6 shows operations included an example process 54 configured (i) to determine a value of a test sample, such as fluid electrical resistance, that corresponds to the hematocrit of the test sample and (ii) to generate acoustic waves having an amplitude, a frequency, and/or a duration that is/are tailored to that value and, thus, to the hematocrit. Process 54 may be performed using the example systems of FIGS. 2, 3 and 5, but may also be performed using other systems such as, but not limited to, those described in U.S. Patent Publication No. 2016/0202237 incorporated by reference above and in U.S. Patent Publication No. 2022/0113297 (Bosy), which was published on Apr. 14, 2022, and which is incorporated herein by reference.

Process 54 includes monitoring (54a) a value based on the hematocrit in the test sample. As explained above, in some implementations, the hematocrit in the test sample is not determined, but rather is inferred from the fluid electrical resistance of the test sample. Accordingly, in example process 54, the value based on hematocrit, is or includes, the fluid electrical resistance. In other implementations, however, the value based on hematocrit may be an actual measurement of the hematocrit. To perform the monitoring (54a), fluid detector 24 determines the voltage difference in test sample 17. This voltage difference is proportional to the fluid electrical resistance of the test sample. Control system 49 receives a measurement of the fluid electrical resistance from fluid detector 24. For example, control system 49 may monitor fluid detector 24 for readings or fluid detector 24 may report its readings to control system 49.

Process 54 includes control system 49 selecting (54b) values of excitation parameters for acoustic transducer 32 based on the value of the fluid electrical resistance determined by fluid detector 24. The values of the excitation parameters may be selected from a LUT as described above or the values of the excitation parameters may be selected by selecting one of multiple drive routines from memory 51. In this example, process 54 selects (54b) a drive routine by comparing (54b1) the determined fluid electrical resistance to a predefined fluid electrical resistance A. If the determined fluid electrical resistance is greater than A, then drive routine 1 is selected (54b2). If the determined fluid electrical resistance is less than or equal to A, then the determined resistance is compared (54b3) to predefined fluid electrical resistance B. If the determined fluid electrical resistance is greater than B, then drive routine 2 is selected (54b4). If the determined fluid electrical resistance is less than or equal to B, then the determined resistance is compared (54b5) to predefined fluid electrical resistance C. If the determined fluid electrical resistance is greater than C, then drive routine 3 is selected (54b6). If the determined fluid electrical resistance is less than or equal to C, then the determined resistance is compared (54b7) to predefined fluid electrical resistance D. If the determined fluid electrical resistance is greater than D, then drive routine 4 is selected (54b8). In this example, if the determined fluid electrical resistance is less than or equal to D (54b9), then drive routine 5 is selected (54b10). Although five comparisons and drive routines are shown, process 54 may contain more than, or fewer than, five comparisons and selectable drive routines, e.g., one, two, three, four, six, seven, eight, nine, and so forth comparisons and drive routines.

Process 54 includes control system 49 controlling (54c) acoustic transducer 32 using the selected values of the excitation parameters, either from the LUT or from the selected drive routine. For example, control system 49 may apply the voltage from the selected drive routine to acoustic transducer 32 to cause acoustic transducer 32 to produce acoustic waves having the selected amplitude; process 54 may apply electrical energy to acoustic transducer 32 to cause acoustic transducer 32 to produce acoustic waves having the frequency from the selected drive routine; and process 54 may apply the voltage and the electrical energy for the duration from the selected drive routine to cause acoustic transducer 32 to produce acoustic waves having the frequency and amplitude from the selected drive routine for the duration.

The acoustic waves cause the red blood cells and plasma to separate, as described herein, thereby producing a cell-free plasma region 36 at a center of the microchannel as shown in FIGS. 2 and 3 or a particle region 44 at a center of the microchannel as shown in FIG. 5. This example uses the cell-free plasma region 36 at the center of the microchannel, as noted above. Accordingly, in this example, cell-free plasma region 36 has a separation width of 70 μm or more and an area corresponding to 2000 pixels or more of the camera in optical detector 34.

Optical detector 34 obtains a measurement of the cell-free plasma region 36, e.g., by capturing an image of the cell-free plasma region. Control system 49 receives (54d) the measurement from optical detector 34. Control system 49 determines (54e) a hemolysis of the test sample by processing the image. For example, control system 49 may inspect the image to estimate the plasma absorbance to detect and to quantify cell free hemoglobin (which represents hemolysis). In example, the system illuminates the microchannel with an LED light source such as light source 28 at e.g., 570 nanometer (nm) and 610 nm light wavelengths, and calculates absorbance at each wavelength following Beer-Lambert's law, where absorbance=$Log_{10}[I_B/I_S]$, and where $I_B$ and $I_S$ are the transmitted light intensity in a process control solution B solution and test sample S, respectively. These absorbance values are translated into the cell-free plasma hemoglobin (hemolysis) level using stored coefficients for hemolysis detection and for flagging blood gas results. The determined presence and/or amount of hemolysis may be output (54f) from the clinical analyzer on a user interface, either graphically or textually, and/or used in other diagnostic processes by the clinical analyzer.

In some implementations, while operations 54b to 54f are occurring, fluid detector 24 may continually, periodically, or intermittently monitor the same test sample for changes in fluid electrical resistance and, thus, changes in hematocrit. Optionally, process 54 may therefore include operation 54g to determine if the hematocrit has changed by comparing a present measurement from fluid detector 24 to the immediately preceding measurement. Optionally, if there has been a change, operations 54b to 54f may be repeated in order to determine a new value for the hemolysis for the same test sample. In some implementations, operation 54g may be omitted.

Figure 7:
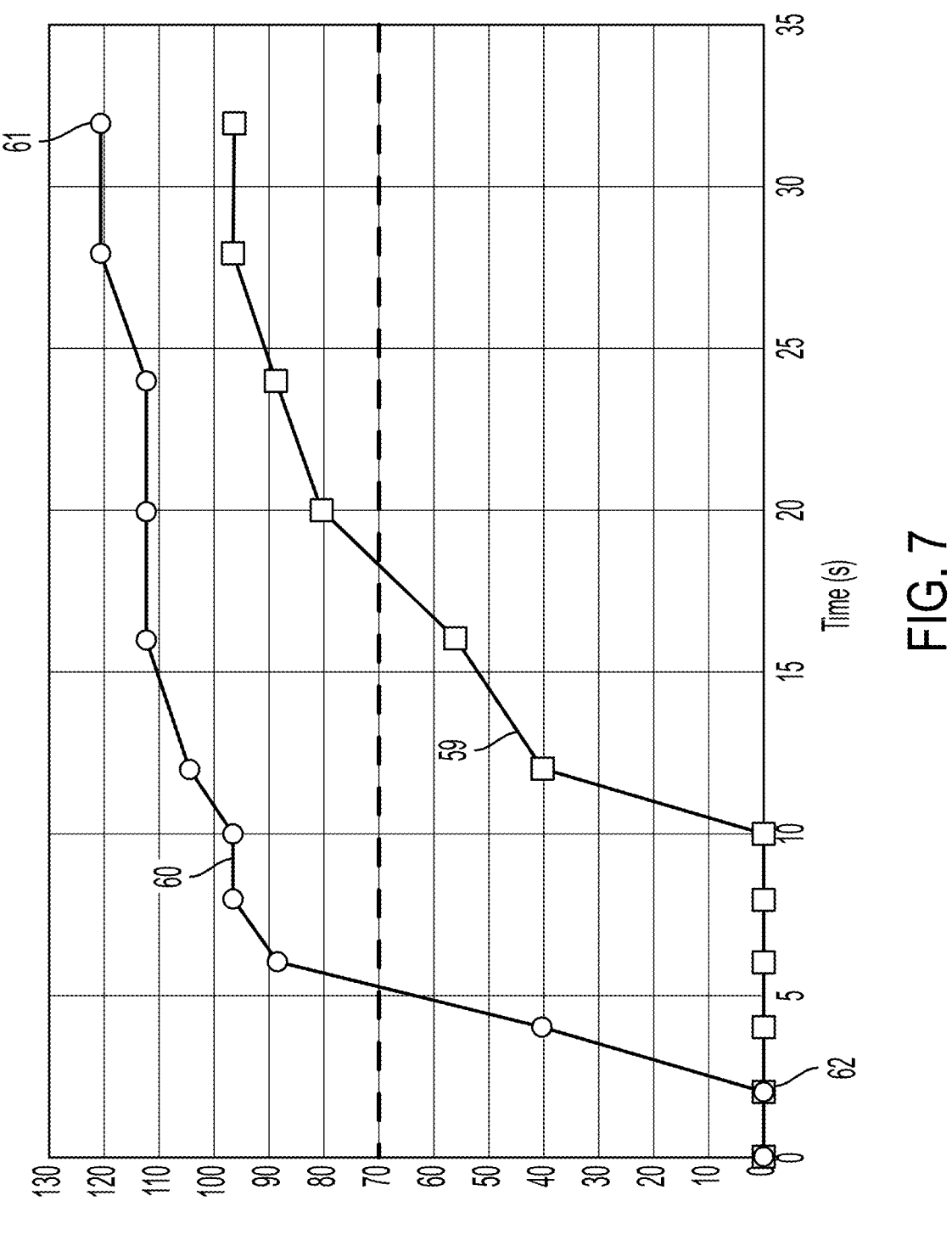
FIG. 7 is a graph showing how the separation width of a cell-free plasma region expands over time using different acoustic transducer excitation parameters.

FIG. 7 is a graph showing how the separation width (plasma width) of a cell-free plasma region expands over time for the same test sample and for acoustic waves having different amplitudes, frequencies, and/or durations. In plot 59, a fixed drive routine was used to drive an acoustic transducer to produce acoustic waves to apply to the test sample. In the fixed drive routine, the excitation parameters have not been tailored to the hematocrit levels. In plot 60, acoustic waves produced using process 54 were applied to the same test sample by the same acoustic transducer, where the excitation parameters were tailored to the sample hematocrit level (as inferred from the samples fluid electrical resistance). As shown, the magnitude of the final separation width is greater 61, and separation begins sooner 62, in plot 60 than in plot 59.

Figure 8:
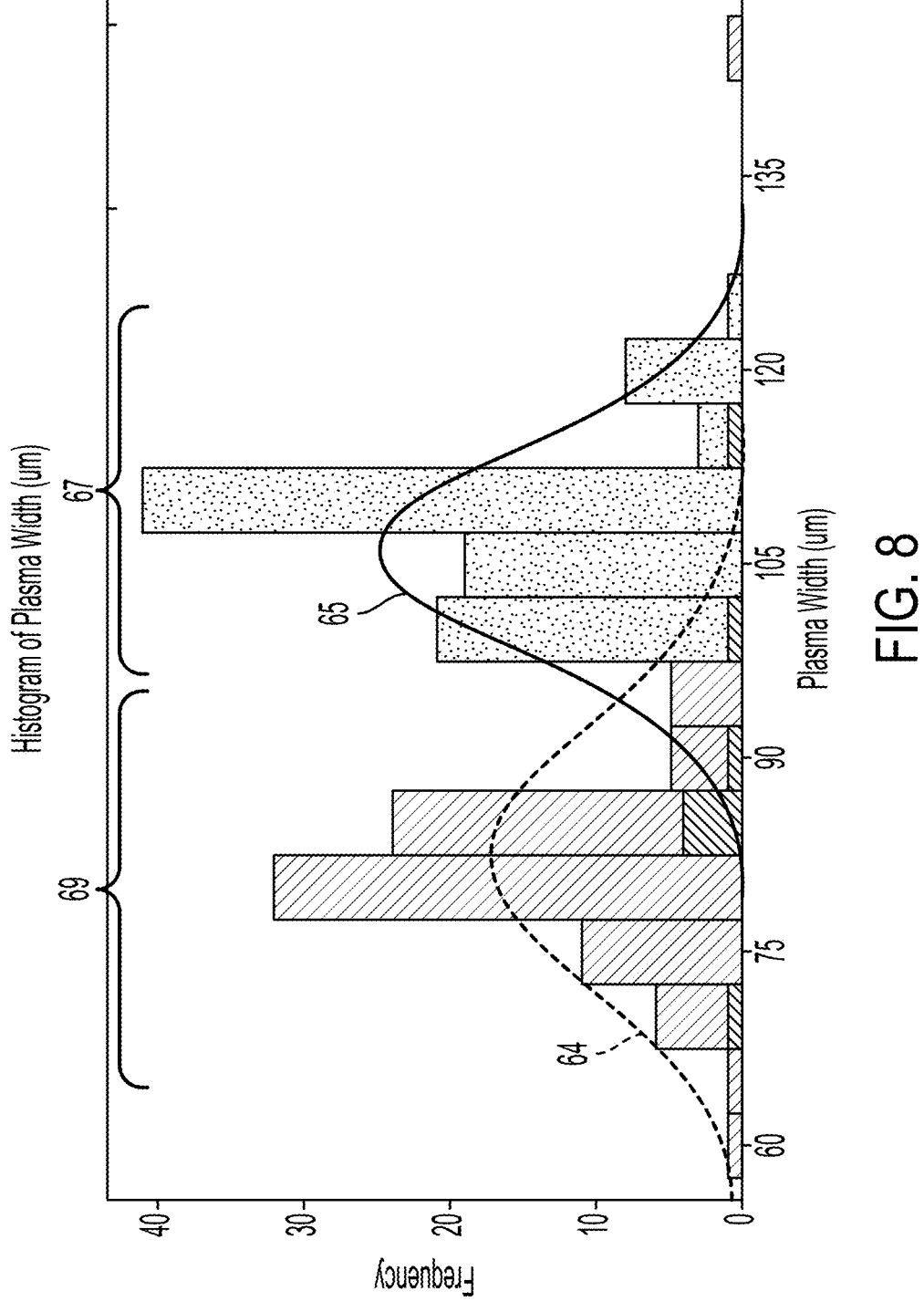
FIG. 8 is a graph showing the relationship between the amplitude of acoustic waves applied by an acoustic transducer to a test sample and the separation width of a cell-free plasma region in that test sample.

FIG. 8 is a graph showing a relationship between the histogram (y-axis frequency=sample counts) of patient blood samples excited by acoustic waves applied by an acoustic transducer and the separation width of a cell-free plasma region in that test samples. FIG. 8 shows the performance 64 of a fixed drive routine used to drive an acoustic transducer. FIG. 8 also shows the performance 65 of acoustic waves produced using process 54. As shown in the figure, the separation widths (plasma widths) 67 for the test samples are mostly greater when acoustic waves produced by process 54 are used than when (69) acoustic wave produced using the fixed drive routine are used.

Figure 9:
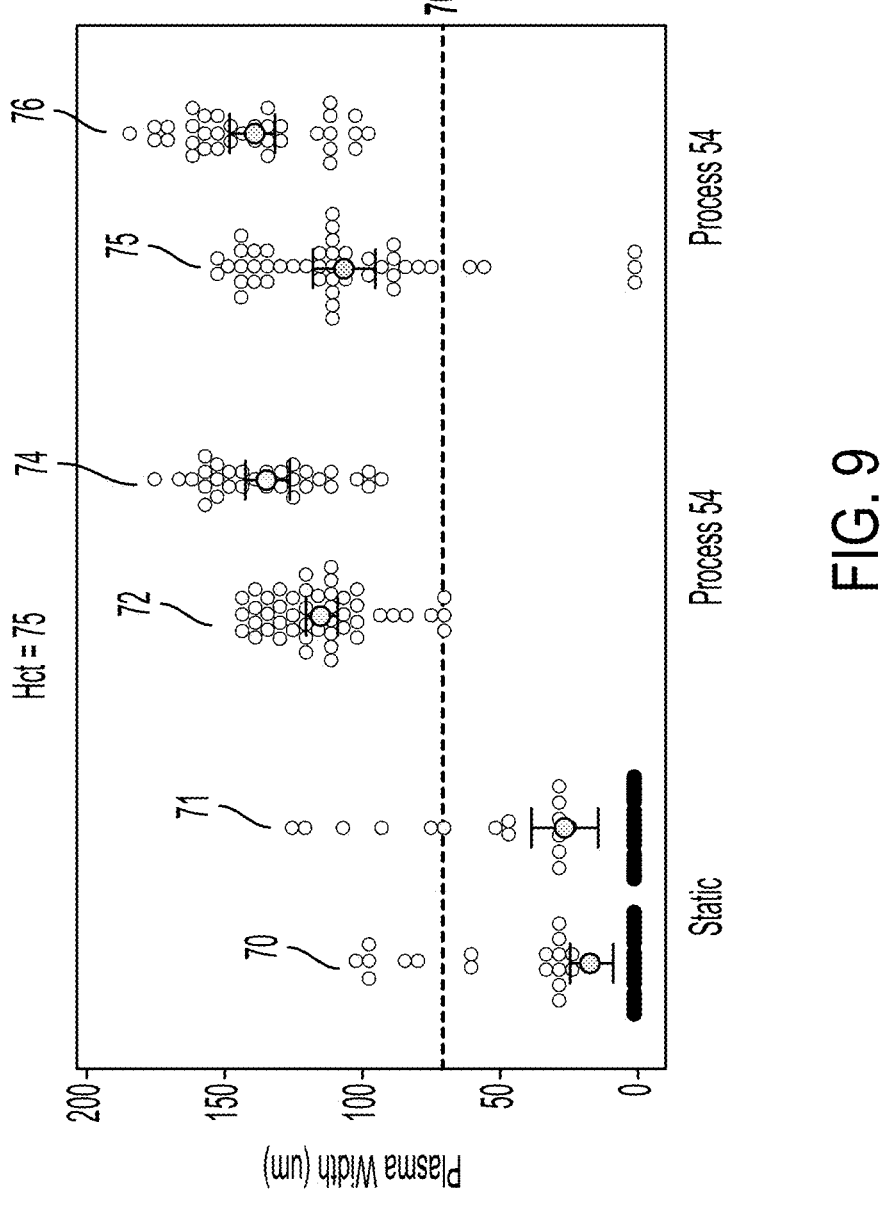
FIG. 9 is scatter plot showing separation widths for an example test sample having a hematocrit (Hct) of 75%, which were produced using acoustic waves generated by a fixed drive routine and which were produced using acoustic waves generated by the process of FIG. 6.

FIG. 9 is a scatter plot showing separation widths for an example test sample having a hematocrit (Hct) of 75%, which were produced by applying excitation parameters from fixed drive routines to an acoustic transducer and which were produced using acoustic waves generated according to the process 54. In examples 70 and 71, acoustic waves produced using the fixed drive routines have a majority of separation widths of less than 70 μm, which may be unacceptable in some implementations. In examples 72, 74, 75, and 76, acoustic waves produced according to process 54 produced a majority of separation widths of greater than 70 μm, which may be desirable in some implementations.

Figure 10:
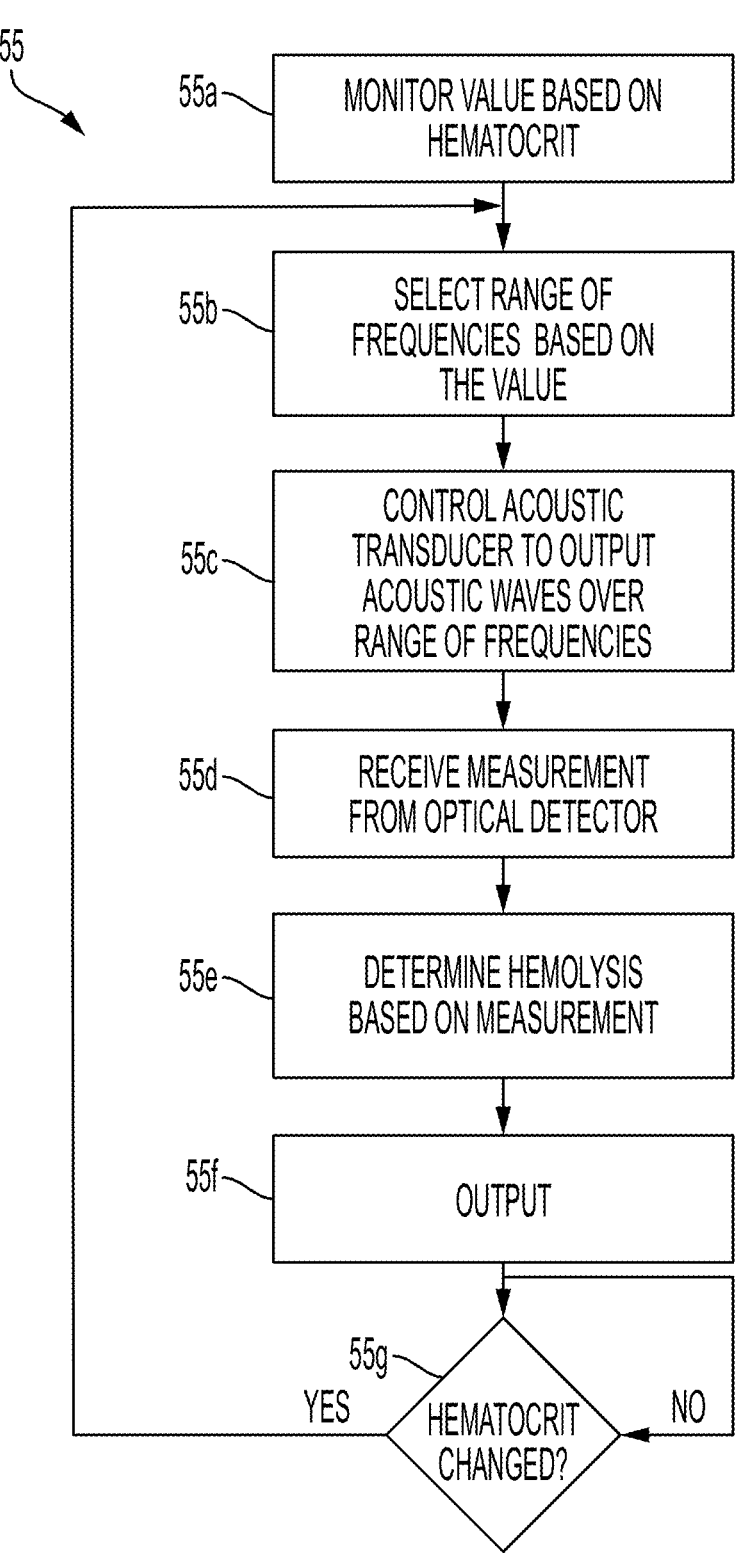
FIG. 10 is a flowchart showing operations included in an example process for controlling an acoustic transducer to separate particles and liquid in a test sample by causing the acoustic transducer to output acoustic waves over a range of frequencies.

FIG. 10 shows operations included an example process 55 configured (i) to determine a value of a test sample, such as fluid electrical resistance, that corresponds to the hematocrit of the test sample and (ii) to generate acoustic waves that sweep across a range of frequencies. Process 55 may be performed using the example systems of FIGS. 2, 3 and 5, but may also be performed using other systems such as, but not limited to, those described in U.S. Patent Publication No. 2016/0202237 and U.S. Patent Publication No. 2022/0113297 (Bosy), which were incorporated by reference.

Process 55 includes monitoring (55a) a value based on the hematocrit in the test sample. Operation 55a may be performed in the same manner as operation 54a of process 54. And, as with operation 54a, the value may be for fluid electrical resistance.

Process 55 includes the control system selecting (55b) a range of frequencies based on the value obtained in operation 55a. This operation may be the same as operation 54b of process 54, except that, in this example, each drive routine may include a different range of frequencies (rather than a single frequency) that the acoustic transducer 32 is to produce, and electrical energies to provide to the acoustic transducer to process those frequencies. These ranges have been previously determined based on testing performed using acoustic transducer 32 for different test samples having different fluid electrical resistances. The ranges have been shown to cause acoustic transducer 32 to produce sufficiently large cell-free plasma regions for optical testing. In some implementations, each range of frequencies includes frequencies greater than 1.85 megahertz (MHz). Different ranges that may be used include, but are not limited to, 1.85 MHz to 1.9 MHz, 1.85 MHz to 1.95 MHz, 1.85 MHz to 2.0 MHz, 1.85 MHz to 2.05 MHz, and so forth. In some implementations, the drive routines may include voltage/amplitude and/or timing/duration values specific to fluid electrical resistances, which may remain constant during frequency sweeps, as described below. In some implementations, the voltage/amplitude and/or timing/duration values may be independent of the fluid electrical resistance of the test sample.

Process 55 includes the control system 49 exciting the acoustic transducer with electrical energy to cause (55c) the acoustic transducer to output acoustic waves that sweep over the range of frequencies in the selected drive routine. The resulting acoustic waves may create a cell-free plasma region, such as region 36 (FIG. 2)

Optical detector 34 obtains a measurement of the cell-free plasma region, e.g., by capturing an image of the cell-free plasma region. Control system 49 receives (55d) the measurement from optical detector 34. Control system 49 determines (55e) a hemolysis of the test sample by processing the image, as described above with respect to operation 54e of process 54. The presence and/or amount of hemolysis may be output (55f) from the clinical analyzer on a user interface, either graphically or textually, and/or used in other processes.

In some implementations, while operations 55b to 55f are occurring, fluid detector 24 may continually, periodically, or intermittently monitor the same test sample for changes in fluid electrical resistance and, thus, changes in hematocrit. Optionally, process 55 may therefore include operation 55g to determine if the hematocrit has changed by comparing a current measurement from fluid detector 24 to the immediately preceding measurement. Optionally, if there has been a change, operations 55b to 55f may be repeated in order to determine a new value for the hemolysis in the same test sample. In some implementations, operation 55g may be omitted.

In some implementations, the drive routines may include ranges for the voltage/amplitude and/or timing/duration values and may vary one or more of those parameters as well while sweeping the frequency or keeping frequency constant.

Figure 11:
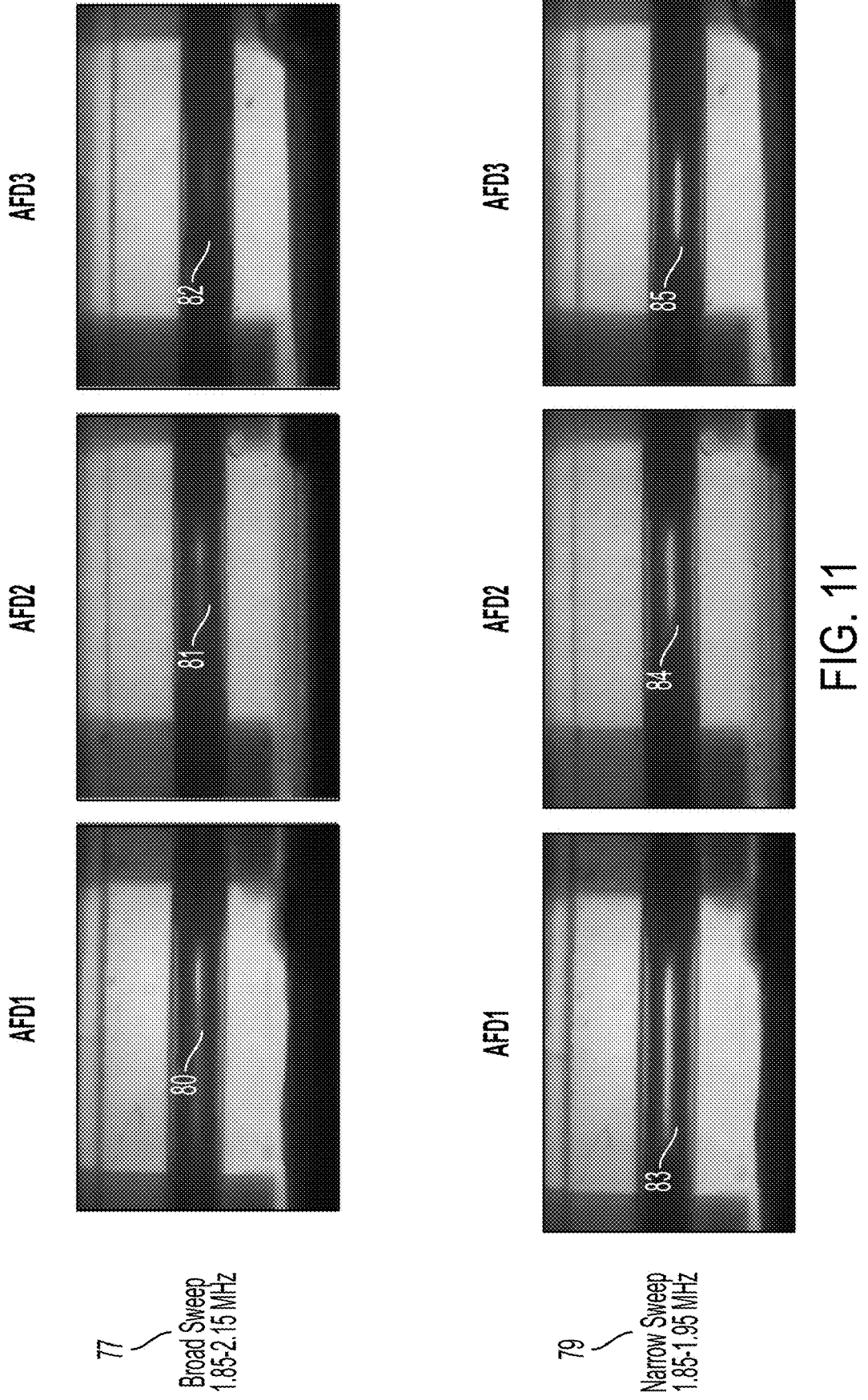
FIG. 11 is a diagram showing different separation widths produced by different acoustofluidic devices (AFD) using different frequency sweeps for the acoustic waves.

FIG. 11 shows example microchannels, each containing a test sample having a hematocrit of 70%. In this example, different AFDs (AFD1, AFD2, and AFD3) have controlled an acoustic transducer to sweep the test sample at different frequency ranges 77 and 79 while keeping the amplitude and duration of the acoustic waves constant. In this example, the frequency ranges are characterized as a broad sweep (77) of 1.85 MHz to 2.15 MHz (79) and a narrow sweep (79) of 1.85 MHz to 1.95 MHz. The frequency sweeps produced different separation widths 80 to 85 in the different AFDs. In this particular example, the narrow sweep (79) of 1.85 MHz to 1.95 MHz produced separation regions that were wider and that have more area than the broad sweep (77) of 1.85 MHz to 2.15 MH.

All or part of the systems and processes described herein including but not limited to processes 54 and 55, and their modifications may be configured and/or controlled at least in part by one or more computers using one or more computer programs tangibly embodied in one or more information carriers, such as in one or more non-transitory machine-readable storage media. A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected.

Actions associated with configuring or controlling the test system and processes described herein can be performed by one or more programmable processors executing one or more computer programs to control or to perform all or some of the operations described herein. All or part of the test systems and processes can be configured or controlled by special purpose logic circuitry, such as, an FPGA (field programmable gate array) and/or an ASIC (application-specific integrated circuit) or embedded microprocessor(s) localized to the instrument hardware.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, such as magnetic, magneto-optical disks, or optical disks. Non-transitory machine-readable storage media suitable for embodying computer program instructions and data include all forms of non-volatile storage area, including by way of example, semiconductor storage area devices, such as EPROM (erasable programmable read-only memory), EEPROM (electrically erasable programmable read-only memory), and flash storage area devices; magnetic disks, such as internal hard disks or removable disks; magneto-optical disks; and CD-ROM (compact disc read-only memory) and DVD-ROM (digital versatile disc read-only memory).

In the description and claims provided herein, the adjectives "first", "second", "third", and the like do not designate priority or order unless context suggests otherwise. Instead, these adjectives may be used solely to differentiate the nouns that they modify.

Elements of different implementations described may be combined to form other implementations not specifically set forth previously. Elements may be left out of the systems described previously without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. A system comprising:
a detector configured to detect a value that is based on a hematocrit of a test sample comprised of plasma and red blood cells;
a fluidic channel configured to hold the test sample;
an acoustic transducer configured to apply acoustic waves to the fluidic channel to separate the plasma from the red blood cells in the fluidic channel, the acoustic waves having at least one of an amplitude, a frequency, or a duration that is based on the value;
memory storing a look-up table (LUT), the LUT storing:
multiple voltages, each voltage corresponding to an amplitude of acoustic waves for a specified value;
multiple frequencies, each frequency corresponding to a frequency of acoustic waves for a specified value; and
multiple durations, each duration corresponding to a duration of acoustic waves to be applied for a specified value; and a control system configured to control the acoustic transducer based on the value, wherein controlling the acoustic transducer based on value comprises:
selecting a voltage from the LUT based on the value;
selecting a frequency from the LUT based on the value;
selecting a duration from the LUT based on the value; and
controlling the acoustic transducer based on the voltage selected, the frequency selected, and the duration selected.

2. The system of claim 1, further comprising:
an optical detector configured to perform optical detection on the plasma separated in the fluidic channel;
wherein the control system is configured to determine hemolysis in the test sample based on a result of the optical detection.

3. The system of claim 1, wherein the value comprises fluid electrical resistance; and
wherein all of the amplitude, the frequency, and the duration of the acoustic waves are based on the fluid electrical resistance.

4. The system of claim 1,
wherein the control system is configured to apply the voltage selected to the acoustic transducer to produce acoustic waves having the amplitude.

5. The system of claim 1, wherein the value comprises fluid electrical resistance that corresponds to a voltage difference between two locations in the test sample, the fluid electrical resistance varying with the hematocrit.

6. The system of claim 1, wherein separating the plasma from the red blood cells in the fluidic channel comprises forming a region of plasma in a center of the fluidic channel.

7. The system of claim 1, wherein separating the plasma from the red blood cells in the fluidic channel comprises forming a region of red blood cells in a center of the fluidic channel.

8. The system of claim 1,
wherein the detector is configured to detect changes over time in the value; and
wherein the control system is configured to control the acoustic transducer to adjust at least one of the amplitude, the frequency, or the duration of the acoustic waves applied to the fluidic channel based on a detected change to the value over time.

9. The system of claim 1,
wherein controlling the acoustic transducer based on the value comprises:
selecting a drive routine from among multiple drive routines stored in memory, the drive routine specifying, for a corresponding value based on the hematocrit, a voltage corresponding to an amplitude of acoustic waves to be produced by the acoustic transducer, a frequency of acoustic waves to be produced by the acoustic transducer, and the duration of acoustic waves to be applied by the acoustic transducer; and
wherein controlling the acoustic transducer based on the voltage selected, the frequency selected, and the duration selected comprises controlling the acoustic transducer in accordance with the drive routine that was selected.

10. The method of claim 1, wherein separating the plasma from the red blood cells in the fluidic channel comprises forming a region of plasma in a center of the fluidic channel; or wherein separating the plasma from the red blood cells in the fluidic channel comprises forming a region of red blood cells in a center of the fluidic channel.

11. A method comprising:

determining a value based on a hematocrit of a test sample comprised of plasma and red blood cells;

applying acoustic waves to a fluidic channel containing the test sample to separate the plasma from the red blood cells, at least one of an amplitude, a frequency, or a duration of the acoustic waves applied to the fluidic channel being based on the value;

performing optical detection on the plasma;

determining hemolysis of the test sample based on a result of the optical detection;

wherein memory stores a look-up table (LUT), the LUT storing:

multiple voltages, each voltage corresponding to an amplitude of acoustic waves for a specified value;

multiple frequencies, each frequency corresponding to a frequency of acoustic waves for a specified value; and multiple durations, each duration corresponding to a duration of acoustic waves to be applied for a specified value; and wherein applying the acoustic waves is controlled by a control system, the control system controlling applying the acoustic waves by performing operations comprising:

selecting a voltage from the LUT based on the value;

selecting a frequency from the LUT based on the value;

selecting a duration from the LUT based on the value; and controlling applying the acoustic waves based on the voltage selected, the frequency selected, and the duration selected.

12. The method of claim 11, wherein the amplitude, the frequency, and the duration of the acoustic waves applied to the fluidic channel are all based on the value.

13. The method of claim 11, wherein the acoustic waves are applied by an acoustic transducer; and wherein controlling the amplitude comprises applying the voltage selected to the acoustic transducer.

14. The method of claim 11, wherein determining the value comprises:

measuring a voltage difference between two locations in the test sample, the voltage difference corresponding to a fluid electrical resistance of the test sample, the fluid electrical resistance varying with the hematocrit.

15. The method of claim 11, wherein detecting the value of the test sample is performed over time; and wherein the method comprises changing at least one of the amplitude, the frequency, or the duration of the acoustic waves applied to the fluidic channel based on a detected change to the value over time.

16. A system comprising:

a detector configured to detect a value that is based on a hematocrit of a test sample comprised of plasma and red blood cells;

a fluidic channel configured to hold the test sample;

an acoustic transducer configured to apply acoustic waves to the fluidic channel to separate the plasma from the red blood cells in the fluidic channel;

a control system configured to control the acoustic transducer to produce acoustic waves that sweep over a range of frequencies, the range of frequencies being based on the value; and memory storing a look-up table (LUT), the LUT storing:

multiple voltages, each voltage corresponding to an amplitude of acoustic waves for a specified value;

multiple ranges of frequencies, each range of frequency corresponding to a range of frequency of acoustic waves for a specified value; and multiple durations, each duration corresponding to a duration of acoustic waves to be applied for a specified value;

wherein the control system is configured to control the acoustic transducer by performing operations comprising:

selecting a voltage from the LUT based on the value;

selecting a range of frequencies from the LUT based on the value;

selecting a duration from the LUT based on the value; and controlling the acoustic transducer based on the voltage selected, the range of frequencies selected, and the duration selected.

17. The system of claim 16, further comprising:

an optical detector configured to perform optical detection on the plasma separated in the fluidic channel; and wherein the control system is configured to determine hemolysis in the test sample based on a result of the optical detection.

18. The system of claim 16, wherein the range of frequencies selected is a first range of frequencies;

wherein the detector is configured to detect changes in the value over time; and wherein the control system is configured to control the acoustic transducer to produce acoustic waves that sweep over a second range of frequencies that is different from the first range of frequencies, the second range of frequencies being based on a detected change to the value over time.

19. The system of claim 16, wherein the range of frequencies selected comprises frequencies greater than 1.85 megahertz (MHz).

* * * * *